United States Patent [19]
Ogawa et al.

[11] Patent Number: 6,152,989
[45] Date of Patent: Nov. 28, 2000

[54] METHOD AND APPARATUS FOR CONCENTRATING SOLUTION

[75] Inventors: Tadao Ogawa; Masayuki Matsui; Takanori Mizuno; Masae Inoue, all of Aichi-ken, Japan

[73] Assignee: Kabushiki Kaisha Toyota Chuo Kenkyusho, Aichi-gun, Japan

[21] Appl. No.: 09/147,449

[22] PCT Filed: Apr. 21, 1998

[86] PCT No.: PCT/JP98/01816

§ 371 Date: Dec. 28, 1998

§ 102(e) Date: Dec. 28, 1998

[87] PCT Pub. No.: WO98/49554

PCT Pub. Date: Nov. 5, 1998

[30] Foreign Application Priority Data

Apr. 28, 1997 [JP] Japan ................................. 9-110812

[51] Int. Cl.[7] .................................................. B01D 15/08
[52] U.S. Cl. .................................... 95/87; 95/245; 96/101
[58] Field of Search ............................ 95/45, 50, 82, 95/86–89, 245; 96/8, 10, 101–108

[56] References Cited

U.S. PATENT DOCUMENTS

| | | | |
|---|---|---|---|
| 3,887,345 | 6/1975 | Pollock et al. | 96/105 |
| 3,920,420 | 11/1975 | Valentin et al. | 96/105 X |
| 4,699,768 | 10/1987 | Weiss | 96/101 X |
| 4,818,264 | 4/1989 | Langhorst | 96/104 X |
| 5,087,360 | 2/1992 | Wright et al. | 96/101 X |
| 5,094,741 | 3/1992 | Frank et al. | 96/101 X |
| 5,250,093 | 10/1993 | Jiang et al. | 96/102 |
| 5,402,668 | 4/1995 | Murakami et al. | 96/104 X |
| 5,607,581 | 3/1997 | Gerner et al. | 96/101 X |
| 5,637,135 | 6/1997 | Ottenstein et al. | 96/108 X |
| 5,779,765 | 7/1998 | Grob et al. | 95/87 X |
| 5,900,532 | 5/1999 | Ikeda et al. | 96/108 X |

OTHER PUBLICATIONS

Patent Abstracts of Japan, vol. 94, No. 11, JP 6–327901, Nov. 29, 1994.
Patent Abstracts of Japan, vol. 96, No. 6, JP 8–143484, Jun. 4, 1996.
Patent Abstracts of Japan, JP 54–145368, Nov. 13, 1979.
Patent Abstracts of Japan, vol. 12, No. 34, JP 62–187250, Aug. 15, 1987.
Tadao Fukuhara, et al., Bunseki Kagaku, vol. 45, No. 5, pp. 421–426, "On–Line System Combining Semimicro LC with $^1$H–NMR Spectrometry", 1996.
Ulla G. Sidelmann, et al., Analytical Chemistry, vol. 67, No. 24, pp. 4441–4445, "750–MHZ Directly Coupled HPLC–NMR: Application to the Sequential Characterization of the Positional Isomers and Anomers of 2–, 3–, and 4–Fluorobenzoic Acid Glucuronides in Equilibrium Mixtures", Dec. 15, 1995.
Varian NMR Instruments, "Separations and Structures", Aug. 1995.
Chuzo Fujimoto, et al., Analytical Chemistry, vol. 64, No. 8, pp. 476–481, "Chromatography/FT–IR Spectrometry Approaches to Analysis", Apr. 15, 1992.

*Primary Examiner*—Robert H. Spitzer
*Attorney, Agent, or Firm*—Oblon, Spivak, McClelland, Maier & Neustadt

[57] ABSTRACT

A solute and a solvent with close boiling points or close polarities are separated and concentrated by vaporizing at least one of the solvent and solute, and selectively adsorbing the vaporized component in an apparatus having a vessel, and an absorbent with an opening into the vessel.

26 Claims, 22 Drawing Sheets

HPLC CHROMATOGRAM OF LIGHT OIL

LIGHT OIL AND HPLC CONCENTRATE OF LIGHT OIL

METHOD AND APPARATUS FOR CONCENTRATING SOLUTION

TECHNICAL FIELD

The present invention relates to a method and a device for removing a solvent from a solution or concentrating a solution for processing a dilute solution of which solute is difficult to be directly detected and qualitatively analyzed by conventional analytical instruments. Especially, the present invention relates to the separation or concentration of the solution where the solute and the solvent have close boiling points or have different polarities with low or nearly the same boiling points. The present device is also used to combine a chromatograph such as high pressure liquid chromatograph (HPLC), a gel permeation chromatograph (GPC) or a super critical fluid chromatograph (SFC) with an instrument for structural elucidation or identification such as infrared spectrometer (IR), or nuclear magnetic resonance spectrometer (NMR).

BACKGROUND ART

As the regulations on automobile exhaust emissions have been strict, higher level analyses or evaluations of fuels are required more than they used to be. For example, microanalysis dealing with trace amounts of compounds such as polynuclear aromatics are required for light oil.

On the other hand, extremely small amount of samples or the samples including low concentration compounds have been routinely analyzed in the field of environmental science. The demand for the analysis with high sensitivity or high selectively also have increased in the other analytical field.

When analyzing these samples, their concentration is important. And, the analytical results depend on the quality of the procedure for concentration. In general, the method of vaporizing the solvent at room temperature or a heated temperature under an atmospheric pressure or a reduced pressure has been used for concentration of the solution samples. For example, an evaporator has been used as a typical concentration method. In addition, the mini-column packed with the packing material for liquid chromatography and so on has recently been used to extract the solute.

In the treatment of low concentration samples, the following problem is likely to arise: the concentration under an atmospheric or reduced pressure loses the solutes where boiling points are close to that of the solvent, and the concentration using the mini-column will dilute the solute to be obtained with a large amount of solvent or makes the solute go away in vapor at recovery.

By the way, automation of the analytical procedures has been promoted and the apparatuses for them have been developed.

The analysis of complex mixture sample is generally classified into pre-treatment, separation, identification and quantitation. The automation of these procedures serves to not only speed-up and labor-saving of the procedures but also improvement of accuracy, sensitivity and reproducibility of analytical results.

Among the above procedures, the method for pre-treatment is varied, depending on the sample conditions or the purposes of analysis. Accordingly, the effect of the automation is little except the case where the similar samples are treated repeatedly. On the other hand, the automation of the procedures in separation, identification and quantitation will be widely used. A typical example of the above automation is GC/MS (gas chromatography/mass spectrometer) in which a gas chromatograph is combined with a mass spectrometer. MS, which is effective in identification and structural analysis of very small amount of organic compounds, has been widely used in the analytical field, since it was combined with GC in 1964. Nowadays, the GC/MS is popularly used as a most powerful analytical systems. However, GC/MS can analyze only the samples which evaporate in GC column (where the temperature is lower than 350° C. and the pressure is lower than 150 kPa). In other words, GC/MS is not applicable to the samples with high boiling point which cannot be separated by this column. As a method for solving the problem, the following method and the like, is employed in which the high boiling point substances are thermally cracked and introduced into GC/MS as low boiling-point substances. However, HPLC, GPC, SFC and so on has generally been used as the separation method for such samples.

The number of the kinds of organic compounds subjected to HPLC is much larger than that subjected to GC, as the number of the kinds of organic compounds exponentially increases with molecular weight.

From the above background, the methods for combining an analytical instrument for identification and structural analysis, such as MS, IR and NMR, with a separation apparatus, such as HPLC, GPC or SFC, have been developed so far.

The most difficult problem in combining HPLC with MS, IR or NMR had been to treat the solvent from HPLC, because the weight of the solvent corresponds to 100 to 1,000 times as much as the carrier gas from GC. It was believed at first that it had been more difficult to combine HPLC with MS than with IR or NMR, because MS must be maintained at a high vacuum. However, contrary to the above prediction, many interfaces for LC/MS were developed. As a result, most LC/MS are more advanced systems than LC/IR and LC/NMR. In most LC/MS interfaces, the solvent from HPLC is used effectively as an ionization-assisting agent.

On the other hand, combining HPLC with NMR, in which a sample is measured in the state of solution, was thought to be easier than with MS. However, the development of the interfaces for LC/NMR were delayed compared with that of LC/MS. LC/NMR systems marketed at present are the same in principle as the system developed first in 1978. Namely, these LC/NMR systems accept HPLC effluent without concentration. In the system, the NMR spectrum of the sample is subtracted with the spectrum of the solvent, which was measured in advance, by the data processing system.

Therefore, the problem that the peaks of solute disappear with the peaks of solvent is likely to arise, when the concentration of the sample is low. The NMR has the lowest sensitivity among the above three analytical instruments. In addition, it has disadvantage that the sensitivity of carbon nuclei ($^{13}C$) which provide important information for the analysis of organic compound, is much lower than that of proton nuclei ($^{1}H$). Accordingly, even in LC/NMR which is commercially available now, the On-Flow measurement is limited to the $^{1}H$-NMR measurement of high-concentration sample.

The development of LC/IR has been further behind LC/NMR. In infrared spectrometer (4,000 to 400 cm$^{-1}$), HPLC solvents such as n-hexane, methylenechloride, chloroform, tetrachloroethane exhibit absorbance at the wave number which is important for analyzing organic compounds. Consequently, the subtraction of the solvent's peaks by data processing system is more difficult in LC/NMR systems. Namely, the solvent must be completely removed by hardware to make LC/IR a practical system Namely, the most serious problem under the development of LC/IR systems and LC/NMR systems were how to eliminate the solvent in the effluent from HPLC.

When we concentrate the effluents from the HPLC, we will be confronted with the following problems.

The first problem arises when the effluents contain the substance where boiling point is low or slightly higher than the solvent. Even if we mildly concentrate such solution under an atmospheric pressure at room temperature, the substance where the boiling point is close to that of the solvent will vaporize with the solvent.

The second problem arises when the effluent from the HPLC is concentrated completely. After complete concentration, the solute becomes high in viscosity and loses its fluidity. In this case, the transfer of the concentrated solute to the subsequent analytical instrument during the concentration becomes difficult. The degree of influence of the decrease in fluidity with concentration differs between LC/NMR and LC/IR.

There is no need to concentrate completely the solution from HPLC as the NMR measures the sample in the state of solution. The HPLC effluent needs to be concentrated up to the level which depends on the sensitivity of NMR. The sensitivity depends on the kind of target nuclei and the measurement mode. That is, NMR is required to continuously transfer enriched effluent to NMR probe, while maintaining a predetermined concentration rate.

On the other hand, on LC/IR, the solvent which is transferred from HPLC needs to be removed completely, because the solvent mostly affects to the IR spectrum.

The GC has been used popularly as an instrument for separating a complex mixture which consists of the substances with the boiling point lower than 350° C. In the GC, substances injected into the column are carried by the carrier gas while they travel reciprocately between the liquid film coated on the inner surface of the column or on the surface of the packing material in the packed column and the carrier gas which flows through the column. The moving rate of the substance depends on its boiling point and its polarity, and gas chromatographic conditions such as the compositions of the liquid film, the temperature of the column and the flow rate of carrier gas. For example, the lower the boiling point of the substance is, or the lower the affinity of the substance to the liquid film is, the faster the substance will be eluted.

As described above, GC is a separation method which has extremely high separating power, which is enough to separate the mixture which consists of the components where the boiling point, polarity or optical activity are slightly different from each other. At the beginning when GC when first developed, the column packed with chemical coated clay or the column packed with polymer had been used as the column. The capillary column, the inside of which is coated and crosslinked with chemicals has generally been used as of late.

Though GC is a method where the separation power is very high, the amount of liquid sample which can be injected is limited to about 10 μL. Accordingly, the amount of the solute which can be recovered after concentration of thin solution less than 1% will be about 0.1 μL in total. If the solute recovered is a complex mixture, the analytical instrument which is able to clear the composition is very limited.

About 1,000 times as much as the sample usually injected for GC (e.g., about 10 mL) must be separated and collected in order to clear the above mixture using the several marketed analytical instruments.

On the other hand, when two kinds of liquid chromatography where the separation mechanisms are different, for instance, the first liquid chromatography (e.g., normal phase HPLC) and the second liquid chromatography (e.g., reverse phase HPLC), are used as a series of chromatography, the performance of the second column in separation will be down, because the solvent from the first column enters into the second column and changes its conditions. Therefore, the second column must be conditioned with a lot of the solvent for the second chromatography in order to recover the original performance of the second column. In addition, in a method where an adsorbed substance is recovered by using back flush, when the back-flushed eluted substance is injected into the next column as it is, since the eluted substance is introduced into the next column together with a large amount of a solvent, there arises an elution layer of a broader band so that a drawback occurs to deteriorate the separating capacity.

The present invention has been developed in view of the aforementioned circumstances. It is therefore an object of the present invention to provide a method which can concentrate a solution containing a solute having a boiling point being close to a boiling point of a solvent, or a solution containing a solute having a polarity being different from a polarity of a solvent, without a loss of the solute so that the solution can be analyzed, and an apparatus for the same; and an apparatus which can make the concentrate obtained by the present method easily connectable with analyzing means to be applied later.

DISCLOSURE OF INVENTION

A method for concentrating a solution according to the present invention is a method for separating and concentrating a solute from a solvent in a solution wherein the boiling points of the solute and the solvent are different from each other or the polarities of the solute and the solvent are different from each other comprising the steps of:

vaporizing at least one of the solvent and the solute; and separating selectively the vaporized at least one of the solvent and the solute using a selectively-adsorbing porous-means which has an ability to selectively adsorb one of the solvent and the solute.

Said selectively-adsorbing porous-means can preferably be at least one member selected from the group consisting of a capillary, an assemble of capillaries, a tube packed with diatomaceous earth or polymer and a porous filter.

The vaporization of at least one of the solvent and the solute can preferably be carried out by heating.

The heating can preferably be carried out at a temperature near the boiling point of the solvent or the solute.

The vaporization of at least one of the solvent and the solute can preferably be carried out with a carrier gas.

Said selectively-adsorbing porous-means can preferably comprise a volume-varying means for controlling the transfer amount of the vaporized solvent and solute.

Said volume-varying means can preferably make one of openings at the end of the capillary, the assemble of capillaries, the tube packed with diatomaceous earth or polymer, or the porous filter between open and close.

The capillary or the assemble of capillaries can preferably have an inner diameter in the range of from 0.1 mm to 1.0 mm. It can further preferably have an inner diameter in the range of from 0.1 mm to 0.3 mm.

The capillary, the assemble of capillaries or the porous filter can preferably be coated with polar on non-polar chemicals on the inner wall thereof. Note that the assemble of capillaries can preferably be formed of hollow fibers which exhibit a chemical resistance to a solution to be processed and whose inner wall is processed by coating with a chemical.

The surface of the diatomaceous earth or polymer in the packed tube can preferably be coated with polar or non-polar chemicals.

The solute captured by said capillary, said assemble of capillaries or said packed tube can preferably be recovered by a solvent whose amount is known.

The solute captured by said capillary, said assemble of capillaries, said packed tube or said porous filter can preferably be recovered by heating said capillary, said assemble of capillaries, said packed tube or said porous filter and with a back flush gas.

A device for concentrating a solution according to the present invention comprises: a vessel for containing a solute and a solvent; and a selectively-adsorbing porous-means having a selective adsorbing ability and having an opening which is opened in the vessel, whereby at least one of the solvent and the solute is vaporized and at least one of the solvent and the solute is transferred through the selectively-adsorbing porous-means.

Said selectively-adsorbing porous-means can preferably comprise at least one of a capillary, an assemble of capillaries, a tube packed with diatomaceous earth or polymer and a porous filter.

Said selectively-adsorbing porous-means can preferably comprise a volume-varying means for controlling the transfer amount of the vaporized solvent or solute.

Said volume-varying means can preferably comprise a pair of cylinder and piston, the cylinder having an inner side surface connected to an opening of the capillary, the assemble of capillaries, or the packed tube, whereby a predetermined number of openings of the capillary or the tube are opened or closed according to the position of piston.

Said volume-varying means can preferably be disposed on a side of the container holding a solution to be concentrated, or on a transfer-side of the vaporized solvent.

Said device can preferably further comprise a heating means and/or carrier-gas introductory port in the vessel for facilitating the evaporation of at least one of the solvent and the solute.

In a bottom surface of said container, a sample take-out unit can preferably be disposed which maintains at a predetermined amount of a solution to be concentrated and supplies a part thereof to an analyzing apparatus at a constant flow rate.

Said take-out unit can preferably be disposed under a first chamber and a second chamber; a solution to be concentrated can preferably be semi-concentrated at the first chamber; and the solution can preferably be concentrated completely at the second chamber.

In said second chamber, the solute which was concentrated completely can preferably be cooled while maintaining it airtight. The second chamber can preferably be an analyzing cell for measuring with an infrared spectrometer, etc.

Said take-out unit can preferably include detecting means for detecting a solvent amount in which a concentrated solution is adjusted at an as-aimed solvent amount.

The take-out unit can preferably include a valve which can recover a concentrated solution by a predetermined solvent amount.

An inner wall of said selectively-adsorbing pore is coated with or cross-linked with a polar or non-polar chemical.

The capillary or the assemble of capillaries can preferably have an inner diameter in the range of from 0.1 mm to 1.0 mm. It can further preferably have an inner diameter in the range of from 0.1 mm to 0.3 mm.

Said porous filter can preferably be an inorganic porous body, and the pore size can preferably be 1.0 mm or less. The pore size can further preferably be 0.5 mm or less.

Hereinafter, the results of an experiment will be described which were the clue to finding out the present invention. FIG. 1 is the results which were obtained by analyzing a hexane solution containing a light oil (10%) with a GC/MS.

During the 30 minutes while the column temperature was kept at 25° C., 1 µL of the light oil solution was injected at intervals of approx. 4 minutes for 4 times. Thereafter, the column temperature was increased to 320° C. in accordance with the program. FIG. 1 is a part of the results.

TABLE 1

| GC Condition | |
| --- | --- |
| Gas Chromatograph: | Capillary Gas Chromatograph (HP-5890A) manufactured by Hewlet Packard Co., Ltd. |
| Amount of Sample/Injection Method: | 1 µL, Split Mode (Split Ratio: 1/80) |
| GC Column (manufactured by Hewlet Packard Co., Ltd.) and Column Programming Condition: | |
| 1.   0.25 mm ø × 30 m, HP-1, 26° C., 30 min., 10° C./min., 320° C., 8 min. | |
| 2.   0.25 mm ø × 30 m, HP-5, 28° C., 30 min., 10° C./min., 300° C., 8 min. | |
| 3.   0.25 mm ø × 30 m, HPWAX, 28° C., 50° C., 100° C., 10° C./min., 230° C. | |
| MS Condition | |
| Mass Spectrometer: | Double-Focusing Mass Spectrometer ZAB-SE manufactured by Micromass Co., Ltd. |
| Ionization: | Electron Impact (70 V, 200 µA) |
| Ion Accelerating Voltage: | 8 kV |
| Mass Range: | 15~400 |
| Ion Detection Voltage: | 2.5 kV |

(Note) As for "GC Column and Column Programming Condition", 1 is applied to each case of FIGS. 1 and 5, 2 is applied to the case of FIG. 6, and 3 is applied to the case of FIG. 7

FIG. 1a shows an amount of all the ions produced by the mass analysis with the vertical axis, and the scanning numbers (1 scanning: about 1.5 sec.) corresponding to the retention times with the horizontal axis. In the all-ion chromatogram, the solvent peak was detected 4 times, which correspond to the number of the sample light oil injections, 4 times, while the column temperature was 25° C. Whilst, the major components of the light oil was detected for the first time after increasing the temperature.

As illustrated by the horizontal axes of FIG. 1a–FIG. 1d, about 2,100 times of scans were carried out to measure the mass spectra in FIG. 1.

FIG. 1b reads out the ion intensity of mass 86, which corresponds to the molecular weight of the solvent, i.e., n-hexane, from the mass spectra, and is referred to as a mass chromatogram. FIG. 1c and FIG. 1d are mass chromatograms which similarly read out the ion intensities of masses 128 and 142, respectively. The mass chromatograms of masses 128 and 142 shown in FIG. 1c and FIG. 1d illustrate how n-nonane, n-decane, naphthalene and methyl naphthalene were eluted, respectively. It is understood that except the peaks derived from n-hexane and n-nonane shown in FIG. 1b and FIG. 1c, the others began to be eluted after the column temperature was increased. Namely, it is understood that the hydrocarbons having a boiling point of decane or more were retained in the 25° C. column. The above results of the experiment was the clue to the present invention.

Here, the amount of the solute obtained by the GC shown in FIG. 1 was extremely small (10%×4 μL<0.4 μL, 0.4 mg or less when the specific gravity was 1 or less). There have been substantially no analyzing apparatuses which could determine the composition explicitly. The sole and capable apparatus is the GC/MS only which provided the data shown in FIG. 1 and FIG. 4 through FIG. 7.

Even when such a trace amount of a solute can be recovered, there are a very few means which can determine the composition explicitly. Accordingly, it is necessary to process a larger amount of solvents. By an apparatus according to the present invention hereinafter described, it is possible to process solutions in an amount as large as about 1,000 times of that of the solution processed by the GC of FIG. 1.

As FIG. 2 illustrates an example of a condensing apparatus according to the present invention in which a container ① for holding a solution before condensation (hereinafter this one is referred to as container 1) and a container ② for receiving a solvent separated from the solution (hereinafter this one is referred to as container 2) are connected by one or more capillaries ③ or a filler pipe (not shown). Thus, only the solvent of the solution to be concentrated is selectively transferred from the container 1 to the container 2 by utilizing the high selecting capacity possessed by the capillaries ③.

The most part of the solutes are present as a liquid phase in the container 1, and a part of the solutes only whose boiling points are close to that of the solvent enters into the capillaries ③, and are captured. These solutes are recovered by back flushing, or the like, to the container 1 with ease. It is possible to again subject the concentrate and the solutes, which are back flushed, to an HPLC as they are.

In the condensing apparatus illustrated in FIG. 2, the constructions and sizes of the container 1 and the container 2 are the same substantially, and their bottoms are formed as a conical shape so that a trace amount of solutes or solvents can be recovered. The side surfaces of the containers are calibrated so that the volumes of the liquids can be read out. The lids ④ are made of a resin in which Teflon packings are bonded together.

The capillaries ③ (10 pieces in the apparatus of FIG. 2) of 0.25 mm in inside diameter and 70 cm in length connect between the two containers 1 and 2. The Teflon-packing lids ④ are provided with holes (airtight between the capillaries and Teflon) for passing the capillaries ③, and the capillaries ③ are passed therethrough.

Here, the capillaries ③, which are inserted into the container 1, are fitted into by about 0.5 cm above the liquid surface of the solution held initially in the container 1. Whilst, assuming that, after the condensation, a solvent is put in a trace amount (in most cases, a couple of hundreds μL) into the container 1 which holds the solutes only in order to back flush, all the capillaries ③, which are inserted into the container 2, are fitted down to the leading end (bottom) of the cone.

Moreover, a fine pipe ⑤ is connected with the container 1 to introduce an inert gas thereinto, inert gas which is for bubbling the solution and vaporizing the same. The fine pipe ⑤ is inserted into the container 1 down to the bottom of the cone so that the last drop of the solvent held in the container 1 can be subjected to the bubbling. A fine pipe ⑥ is connected with the other container 2 to vent a gas so that the pressure inside the container is not increased by the insert gas and solvent coming from the container 1. Note that, in the concentration, the container 2 can be vented by loosening the lid ④. Moreover, the container 2 can be removed so that the solvent passed through the capillaries ③ can be released into the atmosphere. Namely, the container 2 is not essential for the condensation.

In the capillaries after the condensation, a part of the solutes whose boiling points are close to the boiling point of the solvent are retained. By putting a known amount of a solvent into the emptied container 2 and passing the same in the capillaries, all of the solutes entered into the capillaries can be recovered with ease. The loss of the solutes whose boiling points are close to that of the solvent can be made minimum, and can be made into a sample for the next analysis.

Depending on the types of solutes to be subjected to the condensation and the types of solvents to be subjected thereto, the capillaries or filler pipe is changed so that the condensation can cope with a wide range of substances. For example, when concentrating non-polar substances such as hydrocarbons, a capillary coated with a non-polar chemical can be utilized to cope therewith. When concentrating amines of solutions containing highly polar amines, a capillary coated with a polar chemical can be utilized to cope therewith.

Next, a concentrating apparatus is illustrated in FIG. 10 in which capillaries are placed in a constant-temperature chamber and connected with an HPLC. By operating the concentrating apparatus for concentrating a solution under the conditions set forth in Table 2, an eluent which flows in by a flow rate of 2 mL/min. from the HPLC can be completely concentrated in a container 21 in a real time. Namely, the solution coming from the HPLC is introduced into the airtight container 21 by way of a conduit 25, and is heated by a heater block 26 to a temperature corresponding to the boiling point of the solvent while bubbling the solution by helium introduced by way of an inert gas conduit 24. The vaporized solvent is passed through capillaries 23 retained in a constant-temperature chamber 28. Thus, the solvent is taken out by way of a container 22 to carry out a concentrating operation. In the concentrating operation, since the boiling points of the solutes are close to that of the solvent, the capillaries 23 work for capturing and concentrating the low-boiling-point solutes entering into the capillaries 23, and then collect the solutes in the container 21. By the way, the concentrating apparatus of FIG. 10 is for completely concentrating the HPLC eluent and thereafter recovering the same. Accordingly, the concentration speed cannot be adjusted at an arbitrary concentrating rate (between 0 and 100%). Therefore, a method to adjust the concentration speed of the solvent has been investigated.

TABLE 2

| | |
|---|---|
| Chamber: | 50 mm ø × 40 mm |
| Side Surface: | Made of Glass |
| Lid, Bottom Surface: | SUS |
| Chamber Temp. at Bottom: | 70 or 75° C. |
| Carrier Gas, Bubbling Gas: | He, 0.3 L/min. |
| Capillaries: | 0.25 mm ø × 300 mm × 105 pieces |
| Capillaries Temp.: | 0° C., 23° C. |

In the aforementioned solution-concentrating apparatus, the following factors can be considered to affect the concentration speed: the heating temperature of the solution, the heating area, the inner diameter of the capillaries and the number of the capillaries, the controlled temperature of the capillaries, and the flow rate of the bubbling gas, etc. Accordingly, by using this apparatus, an experiment was carried out to concentrate a n-hexane solution containing a light oil, and examined how the heating temperature of the solution, the temperature of the capillaries and the flow rate of the bubbling gas affected. In FIG. 11, the flow rate of an inert gas, helium, is plotted in the horizontal axis, and the bubbling time is plotted in the vertical axis so that the relationship therebetween is illustrated. In FIG. 11, when the heating temperature of the solution (temperature at the bottom of the container) was increased from 70° C. (marked with ▲), corresponding to the boiling point of the n-hexane (69.7° C.), to 75° C. (marked with ●), excepting that the flow rate of the bubbling gas was low (e.g., 0.2 mL/min. or less), it was understood that the concentration speed was hardly changed. And, in the concentration at 70° C., it was understood that a sufficiently high concentration was obtained. Moreover, when the temperature of the capillaries was decreased from 23° C. to 0° C. (marked with ○), as illustrated in FIG. 11, it was also understood that there was no large difference between the concentration speeds.

Whilst, when the flow rate of the bubbling gas was changed in the range of 0.02–0.8 L/min., as illustrated in FIG. 11, it was understood that the time required for the concentration was not changed substantially at the flow rate of 0.2 L/min. or more. According to these results, as for the method for adjusting the concentration speed, the method to change the flow rate of the bubbling gas and the method to change the number of the capillaries were considered effective. However, it is difficult for the former to finely adjust the flow rate. Consequently, as illustrated in FIG. 12, the method to change the number of the capillaries was considered appropriate for the fine adjustment.

However, since the capillaries are fixed to the concentrating apparatus, it is impossible to change the number of capillaries used for concentrating, depending on the types of solvents. Therefore, the concentrating apparatus is provided with volume-varying means for closing one ends of the capillaries so that the total volume of the capillaries to be utilized is adjusted. The volume-varying means, for instance, can adjust the concentration speed by connecting one-end openings of the capillaries with a cylinder inner wall and moving the position of a piston fitted snugly into the cylinder so that a predetermined number of one-end openings of the capillaries are closed to adjust the transfer amount of the vaporized solvent passing through the capillaries. As a result, the solution can be concentrated to a desires solution concentration which can be supplied to analyzing apparatuses connected with the concentrating apparatus as a sample for analysis.

In the aforementioned apparatus, in order to make the solution concentrated to a desired concentration transferable to analyzing apparatuses, the bottom of the concentration container can be provided with a take-out unit. The concentrated sample can be continuously sampled out of the take-out unit. Thus, it is possible to continuously analyze samples.

Further, when the all the pipes, such as the solution conduit, the bubbling gas supply pipe, the capillaries and the concentrated solution recovery pipe, are placed above the concentration container, the concentration container can be formed as a simple configurational construction at the bottom thereof. On the hand, it is difficult to carry out the concentrating operation. Accordingly, the bottom of the concentration container can be provided with a valve as illustrated in FIG. 20 for supplying a bubbling gas and controlling the recovery of the concentrated liquid, and the concentration operation can be simplified by operating the valve.

Furthermore, the take-out unit can be provided with a chamber for keeping the amount of the concentrated liquid constant, and taking out a part thereof at a constant flow rate so that the concentrated liquid of a constant concentrating rate is supplied to analyzing apparatuses.

The aforementioned chamber can be made into two stages. In a first chamber, the concentrated liquid is semi-concentrated. In a second chamber, the semi-concentrated liquid is concentrated completely. And, in the second chamber, the solutes which are concentrated completely are cooled while maintaining it airtight, and can be accommodated therein while maintaining it airtight. Thus, the second chamber can be an analyzing cell for directly measuring with an infrared spectrometer, etc., (FIG. 16, FIG. 17).

The amount of sample separated by an ordinary HPLC is as small as a couple of 10 $\mu$L. Therefore, the amount of the concentrate obtained by the present concentrating apparatus is on this order as well. Accordingly, it is difficult to check the amount of the concentrate with the naked eye. Moreover, since the concentrated substance generally increases the viscosity, it is difficult to recover the concentrate as it is. Consequently, in order to make the trace-amount and viscous concentrate easily recoverable, a trace amount of a solvent is added by way of a solvent conduit 29 illustrated in FIG. 10 to recover it as a solution. In the operation, since the amount of the solvent added is small, the amount of the solvent vaporized at the heating stage 26, which is disposed on the bottom surface of the concentration container, cannot be neglected. Namely, it is difficult to grasp the amount of the solvent which occupies the solution. Accordingly, at the assembling portion of the concentrate in the heating stage 26, there is disposed a cooling water passage 27 so that the solvent recovering the concentrate can be inhibited from vaporizing.

The present apparatus is the one for carrying out the pre-treatment for qualitatively and quantitatively analyzing the solutes which are present in the liquid to be concentrated. Namely, it is intended to continuously supply the concentrate to analyzing apparatuses. Therefore, it is necessary to keep the amount of the concentrated liquid constant in the concentration container so that the amount of the liquid concentrated in the concentration container can be supplied to the subsequent analyzing apparatus at a constant flow rate. Consequently, as means for keeping the amount of the concentrated liquid constant in the concentration container, as illustrated in FIG. 13, a method was found out that in which a dent 33 of a predetermined volume is disposed in the heating stage at the bottom of the concentration container, and the inner wall is covered with a material 34 of low thermal conductivity. With this method, it is made easy to keep the concentrated liquid amount constant by decreasing the vaporization speed of the solvent.

Note that, it is possible to keep the concentrated liquid amount constant, as illustrated in FIG. 21, by placing a photo source and a photoelectric cell at an upper-rim peripheral portion of the dent (a cylinder shape) for accommodating the concentrated liquid, or as illustrated in FIG. 22, a resistance wire of high thermal resistance coefficient or a thermocouple at a predetermined liquid surface.

As for the means for selectively transferring the vaporized solvent only, in addition to the aforementioned capillaries, a porous filter and an assembly of capillaries (i.e., a bundle of hollow fibers) can be employed as well. However, it is preferred to carry out the chemical treatment to the inner wall in the same manner as the aforementioned capillaries. In particular, the porous filter produces an advantage in that, compared with the capillaries, it makes the present apparatus compact.

The inner diameter of the aforementioned capillaries can preferably be in the range of 0.1–1.0 mm. It can further preferably in the range of 0.1–0.3 mm. When the inner diameter of the capillaries is less than 0.1 mm, since the passage resistance is high so that all the solutes move in the liquid phases, the low-boiling-point solutes as well move together with the solvent. Whilst, when the inner diameter of the capillaries is more than 1.0 mm, the portions other than the area where the gas-liquid equilibrium is established are so large that the areas equivalent to the opened state occupy the majority unpreferably.

BEST MODE FOR CARRYING OUT THE INVENTION

First Preferred Embodiment

Figure 3:
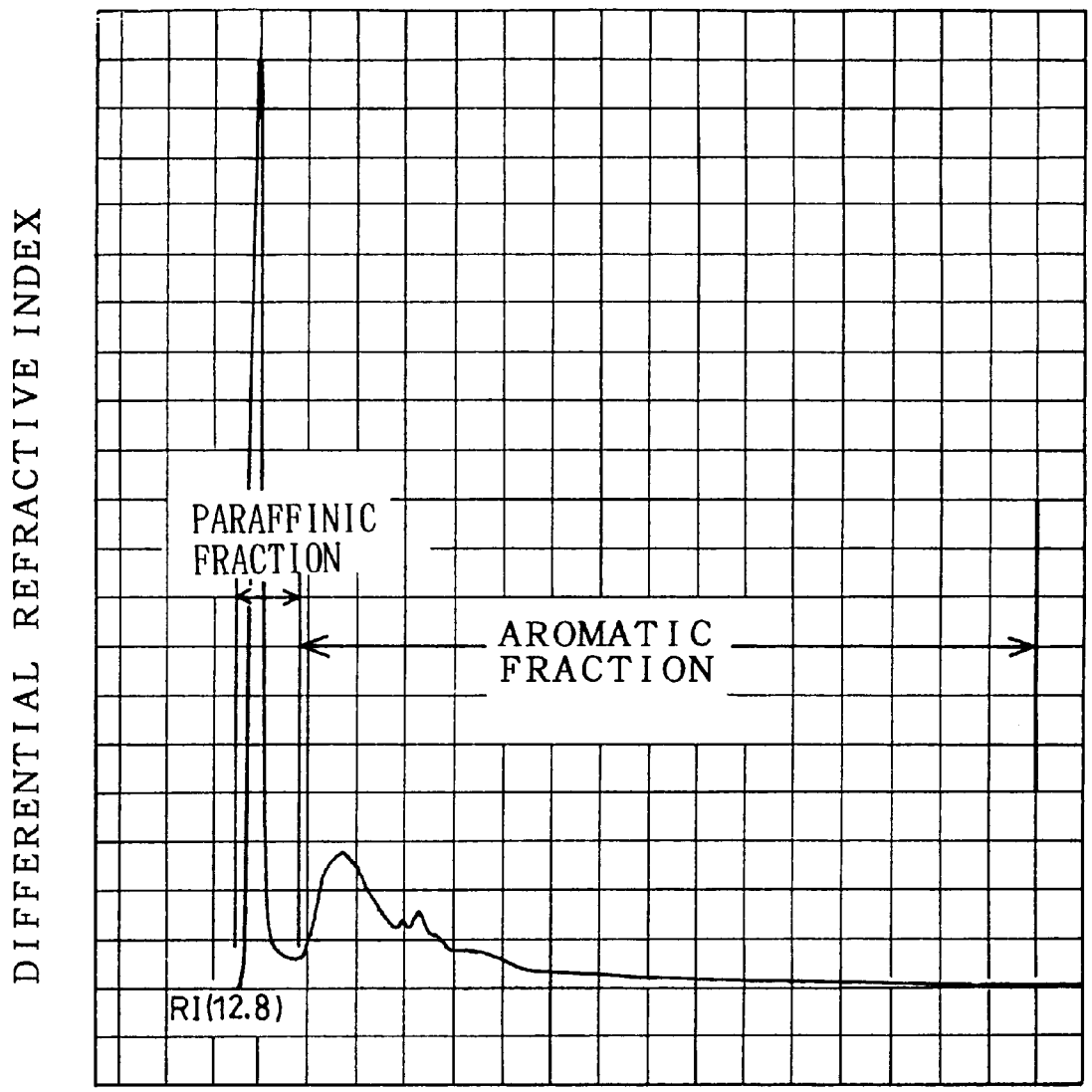
FIG. 3 is an HPLC chromatogram of a light oil.

20 μL light oil substrate was injected into a silica gel column, and a liquid chromatography analysis was carried out under the conditions set forth in Table 3. The results are illustrated in FIG. 3. As illustrated in FIG. 3, the light oil substrate was separated into a paraffin fraction and an aromatic fraction. Accordingly, the paraffin fraction illustrated in FIG. 3 (About 15 μL of solutes was included in 3 mL of this fraction.) was recovered in a container 1 whose inner volume was 14 mL. This operation was repeated 3 times, and each paraffin fraction was recovered in 3 containers 1. Then, the first fraction was concentrated in a draft at room temperature. The second fraction was concentrated by using a concentrating apparatus according to the present invention as hereinafter described. Note that the third fraction was saved as a comparative specimen in an airtight container in order to examine the difference in composition depending on these concentrations.

Figure 1:
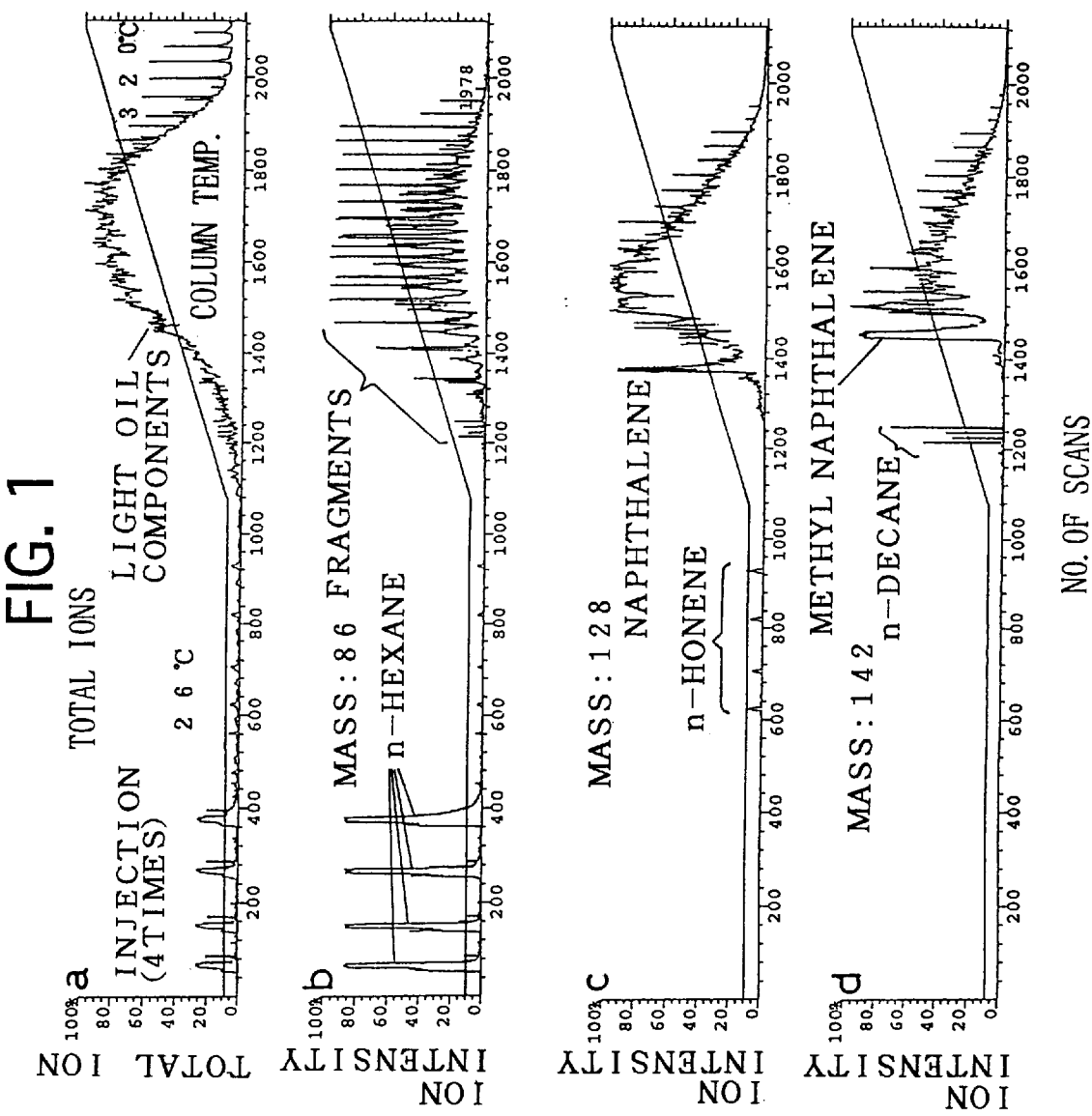
FIG. 1 is the results of a measurement on a light oil by a GC/MS employing a non-polar capillary column, wherein: "a" is a total ion chromatogram illustrating entirely; "b" is a mass chromatogram illustrating how n-hexane was eluted; "c" is a mass chromatogram illustrating how n-nonane was eluted; and "d" is a mass chromatogram illustrating how decane was eluted.
Figure 2:
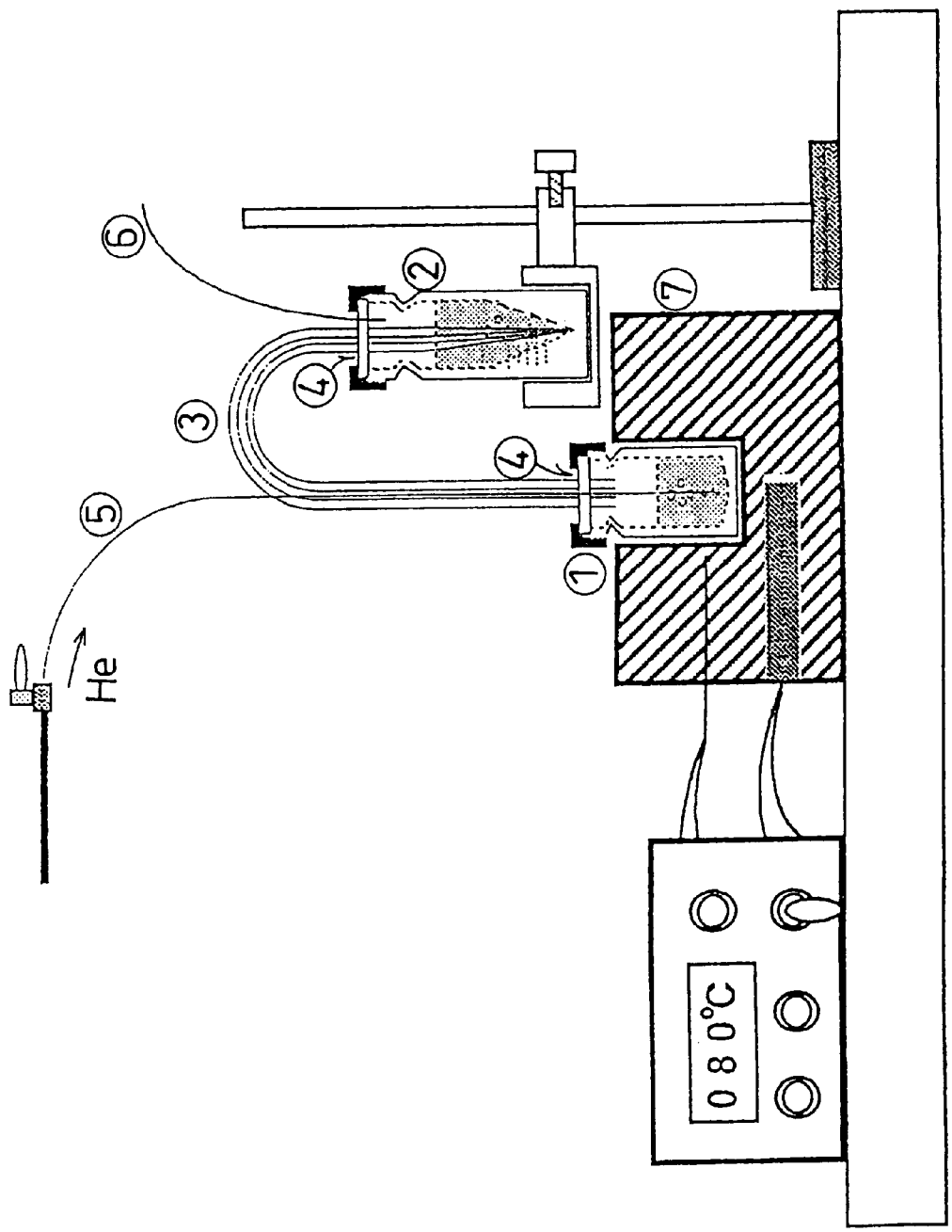
FIG. 2 is a view of an apparatus according to the present invention.

The container 1 holding the second fraction therein was set in a heater block ⑦ made of aluminum shown in FIG. 2. (In the block, a hole, in which ⅔ of the container 1 was accommodated, was formed in advance.) Then, helium for bubbling was introduced into the container 1, and the aluminum heater block ⑦ was heated to 80° C. Note that, in this experiment, the capillaries ③ whose inner wall was coated with cross-linked polydimethylsiloxane were used.

When the solvent of the container 1 disappeared completely, the solvent in the container 2 was thrown away, and clean 50 μL n-hexane was put in the container 2. The helium for bubbling was stopped introducing into the container 1. The container 1 was taken up from the aluminum heater block, and was cooled. By this operation, the 50 μL n-hexane put in the container 2 was passed through the capillaries, and the all amount of the same was entered into the container 1.

Then, the paraffin fraction concentrated at room temperature in air, and the fraction concentrated by the present apparatus were analyzed with a GC/MS, and they were compared with the GC/MS results of the fraction before the concentration.

Figure 4:
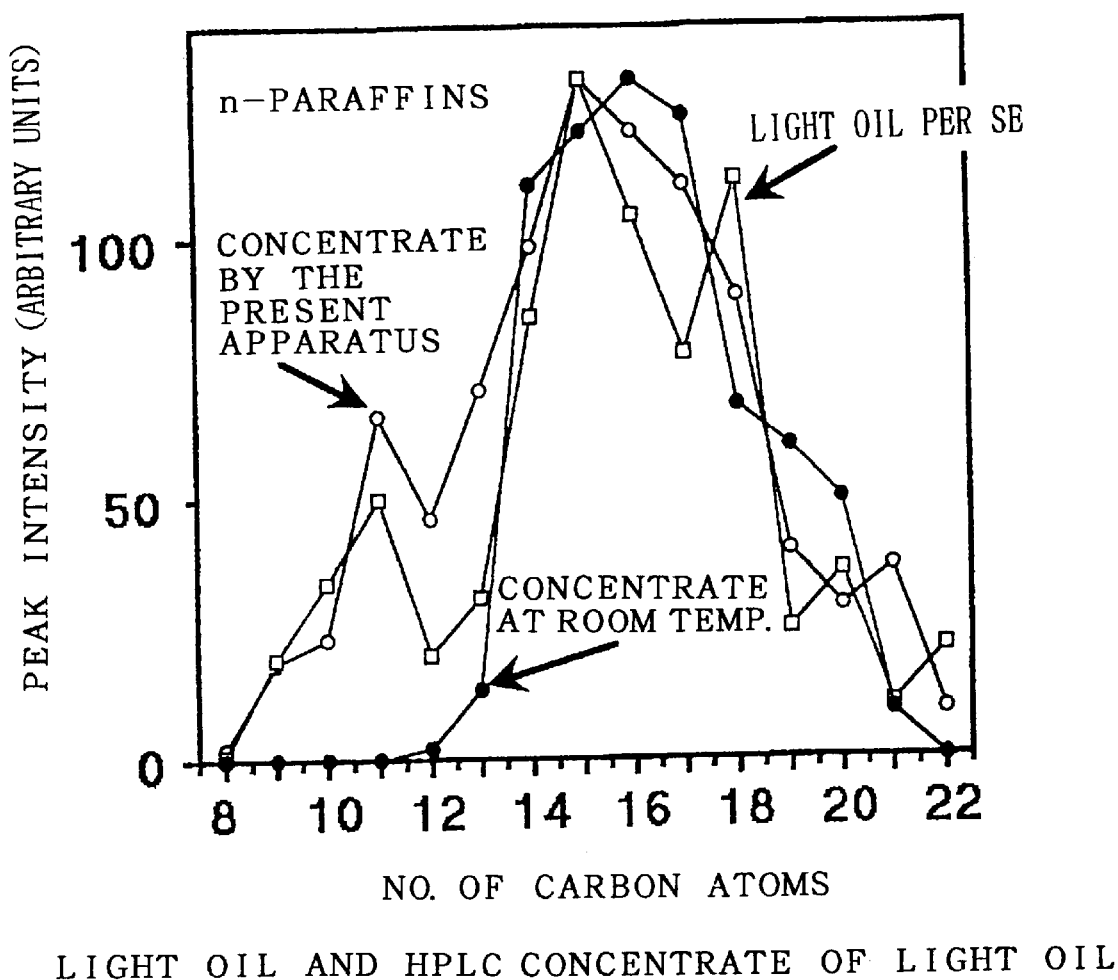
FIG. 4 is a diagram in which the distribution of the number of the carbon atoms in light oil components is plotted.

In FIG. 4, the molecular ion intensities of n-paraffin read out from the results obtained by the GC/MS are plotted with respect to their number of carbon atoms.

In FIG. 34, the preferred embodiment by this apparatus is marked with □, comparative pre-concentration solution is marked with ○, and one concentrated at room temperature in the draft is marked with ●. It is understood that, in the paraffinic fraction which was concentrated at room temperature in the draft, the hydrocarbons whose number of carbon atoms being from 11 to 12 or less were vaporized and were not present. Whilst, it is understood that the fraction, which was concentrated by the method of this preferred embodiment, was substantially identical with the original pre-concentration fraction, and was concentrated without vaporizing the hydrocarbons whose number of carbon atoms were 9 and 10.

Although a variety of separating apparatuses and separating methods have been proposed so far, most of the methods have recovered a larger amount of a solvent along with the solutes than those of solutes. And, a substance whose boiling point is close to that of a solvent, or a substance whose boiling point is slightly lower than that of a solvent vaporizes during the concentration so that it is difficult to recover the same. However, in accordance with this apparatus, in the case that the polarity of a solute is higher than the polarity of a solvent, it is easy to separate and recover a substance whose boiling point is lower than that of a solvent. Moreover, it can be applied to the recovery of the fraction eluted by the super critical fluid chromatography to which engineers' attention has been directed recently.

TABLE 3

Pump: Made by Shimazu Seisakusho, Plunger type
Column: Silica Gel Column, Finepack SIL (Made by Nippon-Bunkoh)
Developing Solvent: n-hexane, 2 mL/min.
sample Conc., Injection Amount: Original Liquid, 20 μL
Detector: Differential Refractometer, UV detector Note that, as for the method for recovering the substances captured by the capillaries or filler pipe, as set forth above, it is possible to carry out a method in which the substances are desorbed by heating the capillaries or filler pipe while flowing a back flushing gas in addition to the method of back-flushing with a solvent which is suitable for the subsequent upcoming analysis.

Second Preferred Embodiment

In the First Preferred Embodiment, the capillaries whose inner wall was coated with cross-linked polydimethylsiloxane were used. However, in the substances whose boiling points are substantially the same but polarities are different with each other, they can be separated by using capillaries whose inner wall is coated with a polar substance, for example, polyethylene glycol, etc.

Figure 5:
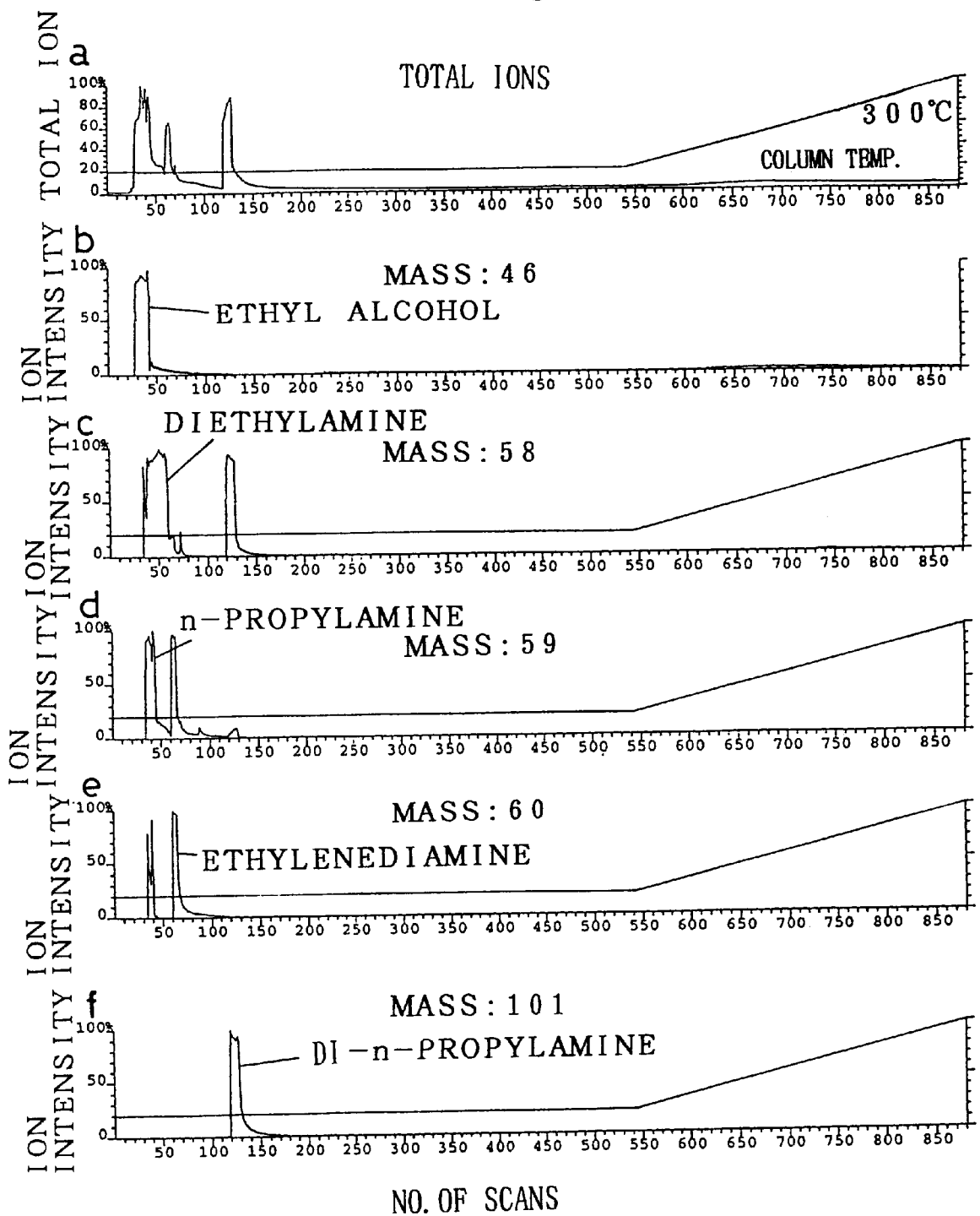
FIG. 5 is the results of a measurement on amines by a GC/MS employing a non-polar capillary column, wherein: "a" is a total ion chromatogram illustrating entirely; "b" is a mass chromatogram illustrating how ethyl alcohol was eluted; "c" is a mass chromatogram illustrating how diethylamine was eluted; "d" is a mass chromatogram illustrating how n-propylamine was eluted; "e" is a mass chromatogram illustrating how diethyleneamine was eluted; and "f" is a mass chromatogram illustrating how di-n-propylamine was eluted, respectively.
Figure 6:
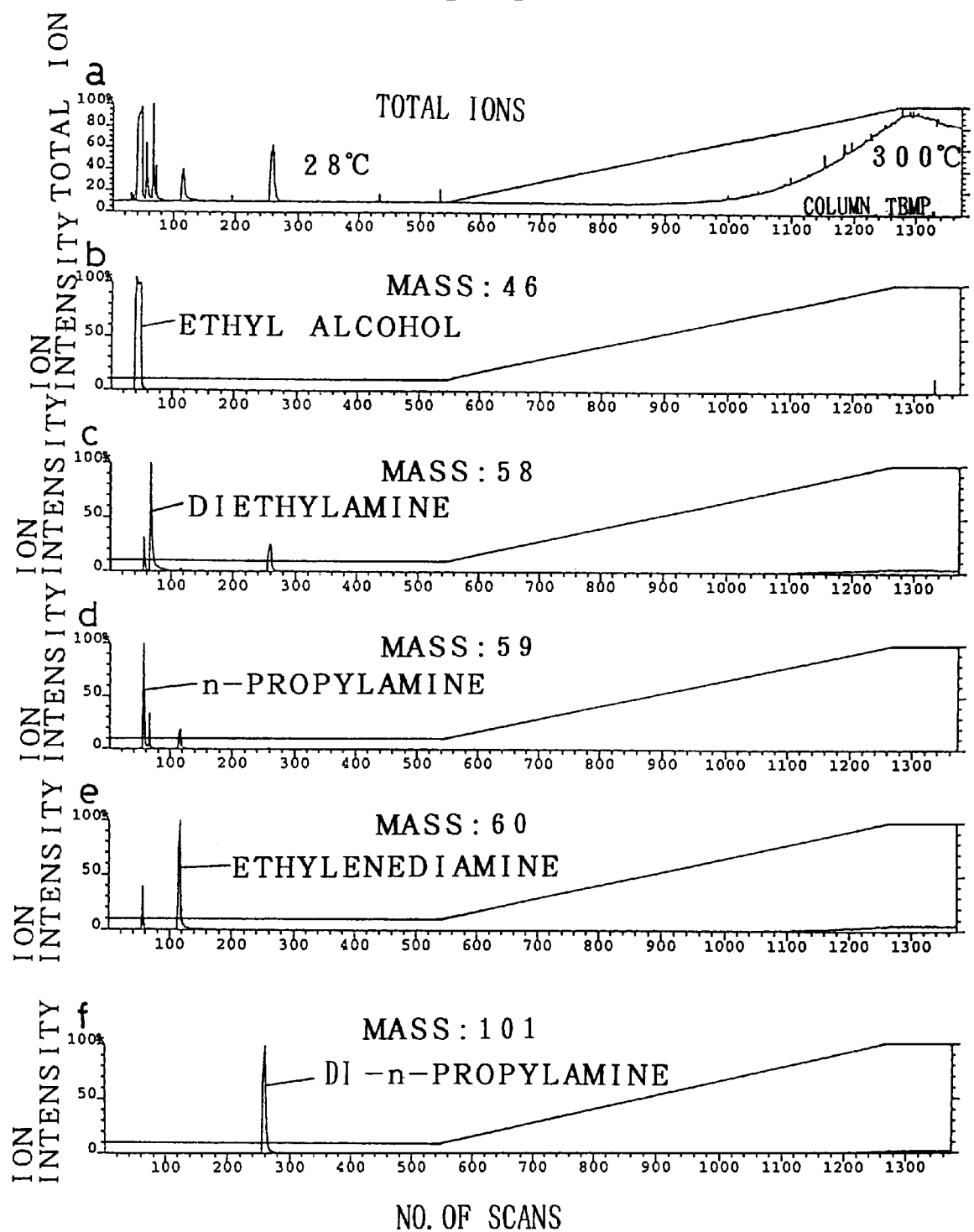
FIG. 6 is the results of a measurement on amines by a GC/MS employing a slightly polar capillary column, wherein: "a" is a total ion chromatogram illustrating entirely; "b"is a mass chromatogram illustrating how ethyl alcohol was eluted; "c" is a mass chromatogram illustrating how diethylamine was eluted; "d" is a mass chromatogram illustrating how n-propylamine was eluted; "e" is a mass chromatogram illustrating how diethyleneamine was eluted; and "f" is a mass chromatogram illustrating how di-n-propylamine was eluted.
Figure 7:
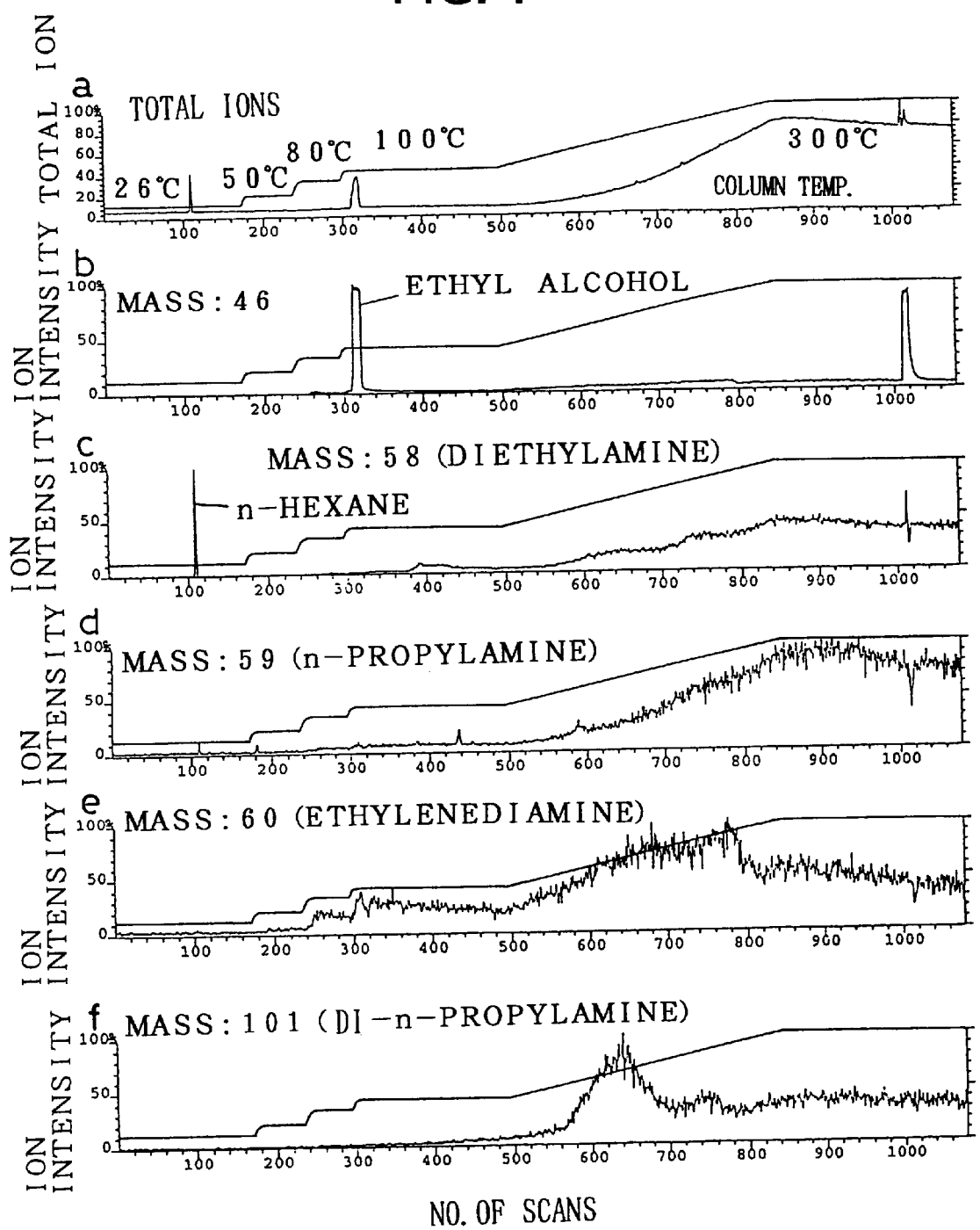
FIG. 7 is the results of a measurement on amines by a GC/MS employing a highly polar capillary column, wherein: "a" is a total ion chromatogram illustrating entirely; "b" is a mass chromatogram illustrating how ethyl alcohol was eluted; "c" is a mass chromatogram illustrating how diethylamine was eluted; "d" is a mass chromatogram illustrating how n-propylamine was eluted; "e" is a mass chromatogram illustrating how diethyleneamine was eluted; and "f" is a mass chromatogram illustrating how di-n-propylamine was eluted.

FIG. 5–FIG. 7 illustrate the results of separations tried by using three types of capillary columns and an ethyl alcohol solution in which an amine mixture was solved and whose composition is set forth in Table 4.

TABLE 4

| Amine | Boiling Point | Amount |
| --- | --- | --- |
| ethylenediamine | 117° C. | 180 μL |
| diethylamine | 56° C. | 180 μL |
| di-n-propylamine | 110° C. | 180 μL |
| n-propylamine | 49° C. | 180 μL |
| ethyl alcohol | 78° C. | 1 mL |

FIG. 5a through FIG. 5f are chromatograms which were carried out by the non-polar capillary column whose inner wall was coated with the cross-linked polydimethylsiloxane. FIG. 5a is an all-ion chromatogram, and FIG. 5b through 5f are mass chromatograms for illustrating how the amines were eluted. As illustrated in FIG. 5a, at the column temperature of 28° C., it is understood that all the substances were eluted at the substantially same retention time and were hardly separated. FIG. 5b illustrates how the ethyl alcohol was eluted. FIG. 5c illustrates how the diethylamine was eluted. FIG. 5d illustrates how the propylamine was eluted. FIG. 5e illustrates how the ethylenediamine was eluted. FIG. 5f illustrates how the dipropylamine was eluted. In these, all of them were eluted within the scanning No. 150 (the scale of the horizontal axis).

Whilst, in the column whose inner wall was coated with polydimethylsiloxane containing a diphenyl groups of 5%, as illustrated in FIG. 6a through 6f, it is seen that peaks of some of a part of the substances overlapped, but it is understood that a part of the peaks were separated. Especially, the n-propylamine (FIG. 6d) and the diethylamine (FIG. 6c) whose boiling points are lower compared with that of the ethyl alcohol (FIG. 6b) were eluted later than the ethanol. Thus, in this column, it is understood that the separation was strongly governed by the polarities of the substances. However, in order to elute all of the substances at the column temperature of 28° C., it is understood that this solution could not be concentrated under this condition. For example, it is necessary to decrease the column temperature until only the ethyl alcohol can be eluted. However, according to FIG. 6, it is difficult to completely separate the diethylamine and the n-propylamine. Accordingly, it is judged that it is difficult to completely suppress the vaporization of these amines.

On the other hand, the results analyzed by a capillary column whose inner wall was coated with polyethylene glycol of high polarity are illustrated in FIG. 7a through FIG. 7f. As illustrated in FIG. 7a, while the column temperature was between 26° C., 50° C. and 80° C., except hexane (FIG. 7c) being the impurity in the solvent, no eluted substances were seen. At the column temperature of 100° C., only the ethyl alcohol (FIG. 7b), the solvent, was eluted for the first time. Whilst, the four compositions (FIG. 7d through FIG. 7f and FIG. 7g) of the amines were not eluted even when the column was at 230° C. Namely, it is understood that the amines, i.e., the solutes, were completely captured in the column.

Therefore, by using the polar capillary column as the capillaries of the concentrating apparatus, the solutes, i.e., the amines set forth in Table 4, and the solvent, i.e., the ethyl alcohol, can be separated completely. In the separation, since most of the amines are considered being captured in the capillaries, it is necessary to back flush with a solvent having high solubility to the amines. As described above, in the Second Preferred Embodiment, even a substance whose boiling point is lower than that of a solvent can be separated from the solvent when the substance exhibits high polarity.

As described above, in the two preferred embodiments, the case is taken up where the solvent is the substance moving in the capillaries. However, it is natural that, even when the substance passing in the capillaries is a solute, for instance, a trace-amount substance in a solution, the same can be separated and concentrated similarly. However, in this case, it is necessary to cool the passing liquid so that it does not vaporize from the container 2.

Third Preferred Embodiment

Figure 8:
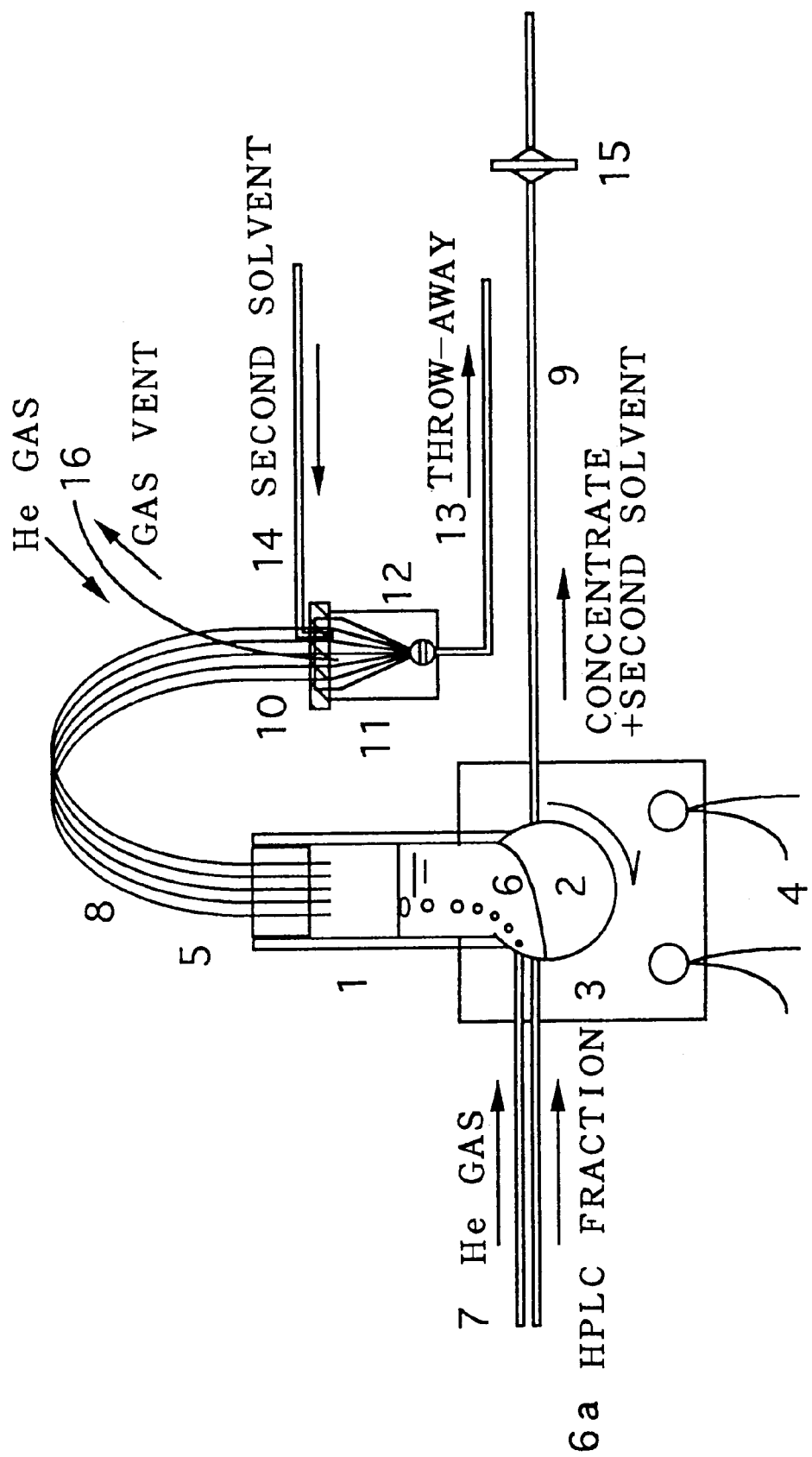
FIG. 8 is a view of the arrangement of an interface for an HPLC of a Third Preferred Embodiment according to the present invention.

This preferred embodiment is one in which the apparatus of FIG. 2 is combined with a HPLC, such as a normal phase and a reverse phase, whose separation mechanisms differ with each other. Namely, it is made applicable as an interface for a multi-dimensional HPLC. FIG. 8 is the explanatory view. To the bottom of a cylinder 1, there is attached a rotary valve 2, a part of which is machined out as a concaved-surface-lens shape 6. The cylinder 1 and the concaved surface 6 of the rotary valve 2 accommodates an eluent coming from a first column, and thereby forms a concentration filed 6. Over the rotary valve 2, a pipe 6a for introducing the eluent coming from the first column, a pipe 7 for introducing an inert gas for bubbling the eluent to concentrate the same, and a pipe 9 for feeding out concentrated solutes and a second HPLC solvent are connected as illustrated in FIG. 8. The upper portion of the cylinder 1 is closed by a plug 5 which is made of a silicone rubber or a fluororubber which is coated with Teflon. Into the Teflon-coated rubber plug 5, 12 pieces of capillaries 8, which are similar to those used in the First and Second Preferred Embodiments, are inserted. The capillaries 8 connect between a concentration chamber 6, which is constituted by the cylinder 1 and the rotary valve 2, and a container 11 for receiving a transferred solvent. The bottom block 3 and the rotary valve are heated by a heater 4 for heating the solution. Further, all of the 12 pieces of the capillaries, which are inserted into the Teflon-coated packing 10 of the container 11, are inserted down to the cone-shaped bottom of the container 11. With this arrangement, it is possible to back flush the substances in the capillaries with a small amount of a solvent supplied from the port 14. Furthermore, in the container 11, a rotary valve 12 for abolishing the transferred solvent is disposed at the bottom portion, and a capillary 16 for venting a gas is attached so that it penetrates through the Teflon-coated packing 10.

Figure 9:
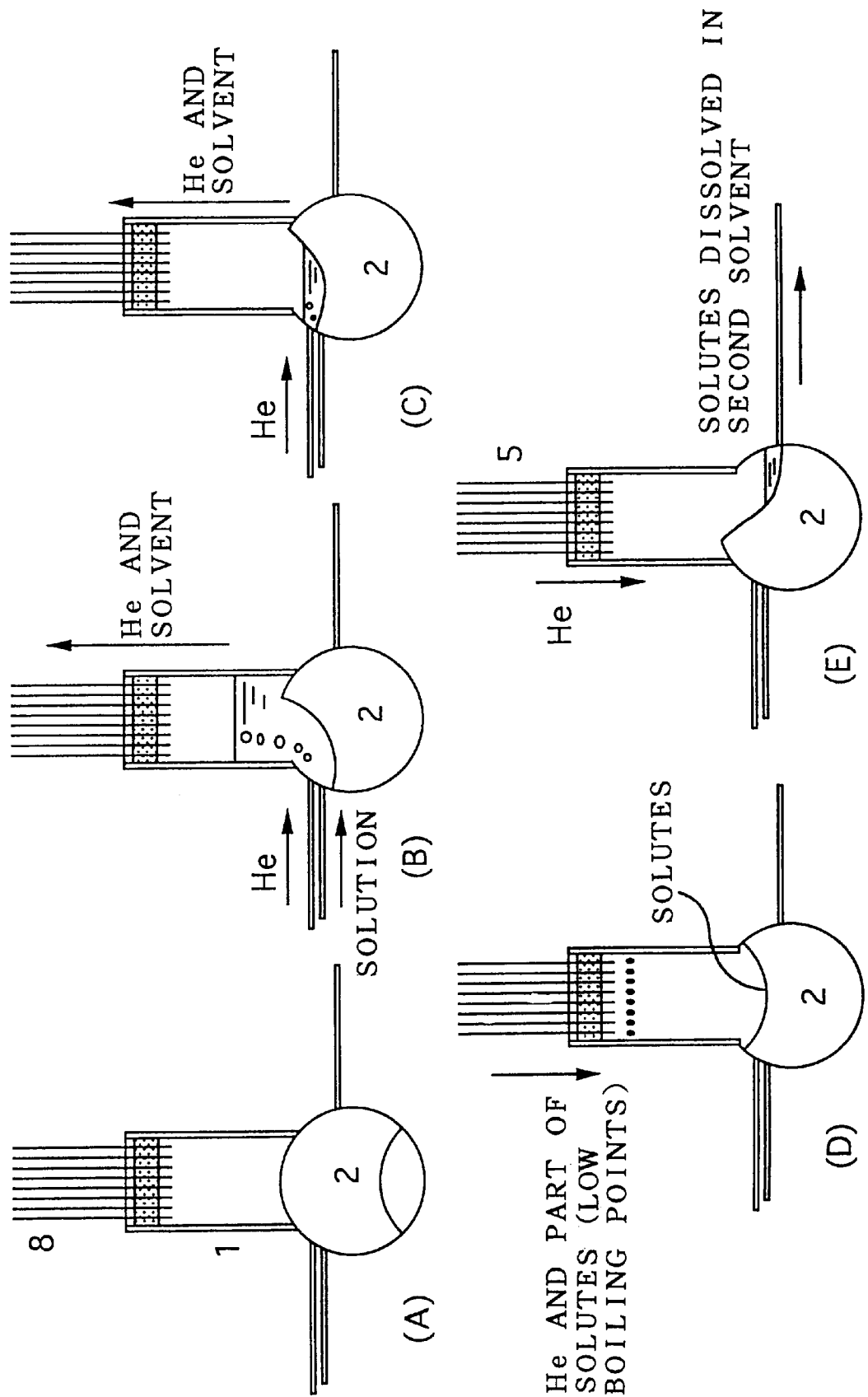
FIG. 9 is an explanatory diagram for illustrating the operation processes (from "A" to "E") of a rotary valve of the interface for an HPLC of the Third Preferred Embodiment according to the present invention.

Hereinafter, an example of the operations of the rotary valve 2 will be described (FIG. 9).

First, in the first HPLC, when the peak of a noted substance is detected, the rotary valve 2 is rotated from the state of "A" to the state of "B", and thereby the eluent coming from the first column and the He gas for bubbling are fed into the concentration chamber 6. In the first HPLC, when the peak of the noted substance is finished, the rotary valve 2 is rotated to the state of "C", and thereby only the He gas is introduced. When it is confirmed by observing the bottom surface (namely, the concaved surface of the rotary valve) of the concentration chamber 6 that the eluent is concentrated completely, the rotary valve 2 is further rotated to the position of "D". Then, into the container which is emptied by throwing away the solvent coming from the container 1, an accurately measured amount of a solvent (the second HPLC solvent) is put in, and the back-flushing He gas is fed by way of the gas-venting capillary 16. In the state of "D", an operator waits until the concentrate on the concaved surface of the rotary valve dissolves. When the solutes dissolve completely, the rotary valve 2 is rotated to the position of "E", and thereby the solutes dissolved in the second solvent are fed into a sample-injecting loop of the second HPLC by way of the pipe 9 and the filter 15. Thus, the eluted substances coming from the first HPLC can be prepared as a sample for the second HPLC, sample which uses a different solvent from that of the first HPLC. Hence, an interface for a multi-dimensional HPLC can be formed.

Fourth Preferred Embodiment

Figure 12:
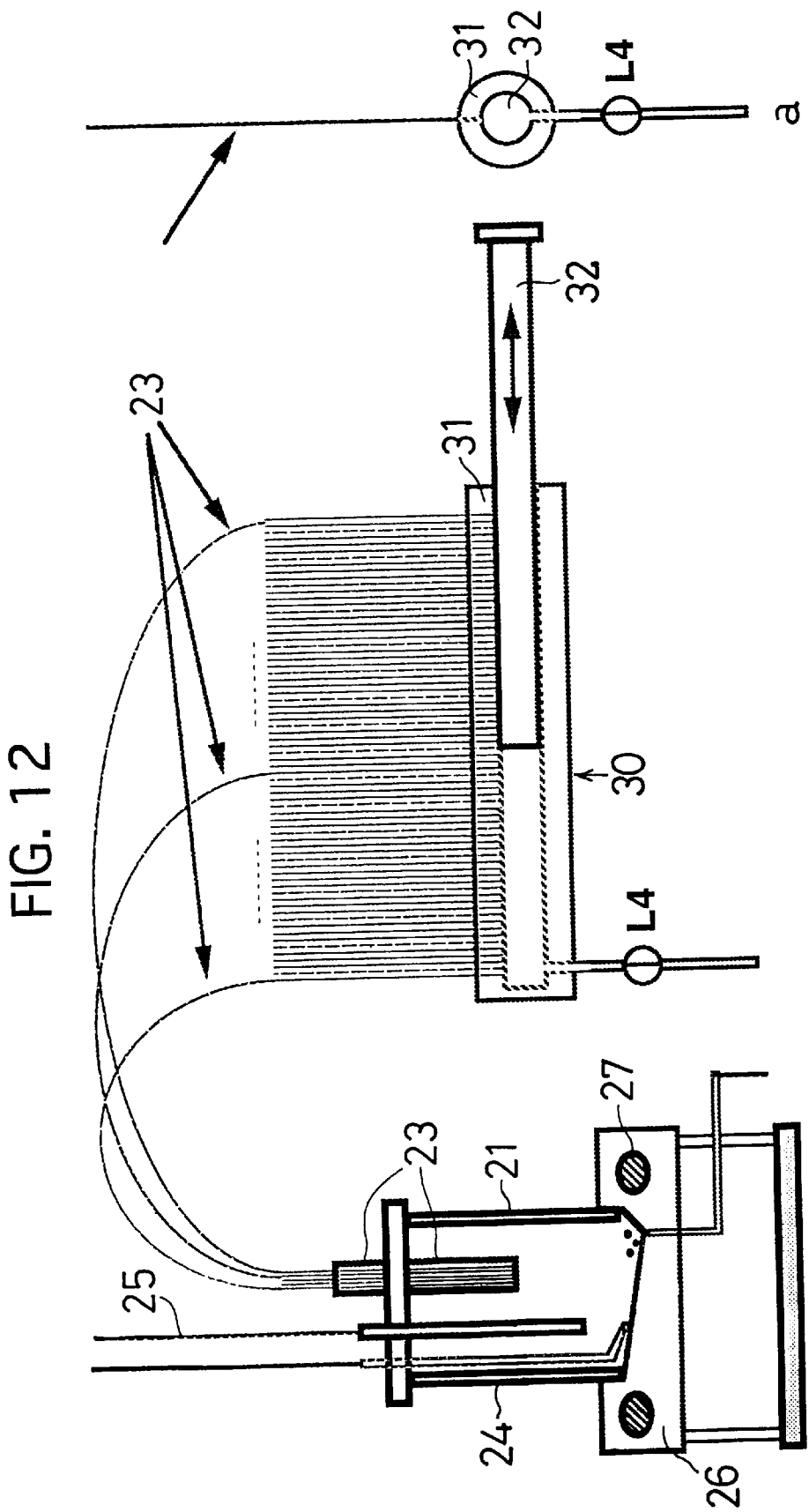
FIG. 12 is a view for describing volume-varying means of a concentrating apparatus of a Fourth Preferred Embodiment according to the present invention; wherein FIG. "a" is a side view of the volume-varying means.

FIG. 12 illustrates a system for feeding a sample into an NMR while concentrating an HPLC eluent. In the bottom surface of the solution-concentrating container of the concentrating apparatus for a solution, concentrating apparatus whose basic portions are described in FIG. 10, there is disposed a take-out opening for recovering a concentrate. In the upper portion of this container 21, an introduction opening 25 for an HPLC eluent, an introduction opening 24 for a bubbling gas and capillaries 23 for evacuating a vaporized solvent are connected. According to experiments, it is understood that the vaporization speed of the solvent can be easily controlled by closing a part of the end openings of the capillaries which are connected with the container. Accordingly, on the downstream side of the capillaries 23 going out from the concentration container, volume-varying means 30 illustrated in FIG. 12 is connected.

This volume-varying means 30 is arranged so that the end openings of a plurality of capillaries (for example, 105 pieces) 23 are connected with a cylinder-shaped cylinder 31, and so that an arbitrary number of the openings of the capillaries are closed with the top surface of a piston 32 by the positional movement of the piston 32 which is inserted into the cylinder 31. By the volume-varying means 30, an arbitrary number of the outlets of the capillaries 23 (e.g., from 1 to 105 pieces of the same) can be closed, and accordingly the concentration speed of the solvent can be adjusted. Moreover, the cylinder 31 serves as a receiver for the vaporized liquid. As illustrated in the side view of FIG. 12a, the evacuation of the vaporized liquid is carried out by a valve (L4).

Here, the concentrating rate of the concentrated liquid fed out to the NMR from the bottom of the heating container can be obtained by the flow rate of the HPLC and the flow rate of the solvent going out from the receiver. Note that the airtightness between the piston 32 and the cylinder 31 of the volume-varying means 30 is maintained by, for example, an O-ring which is made of a perfluororubber.

Figure 13:
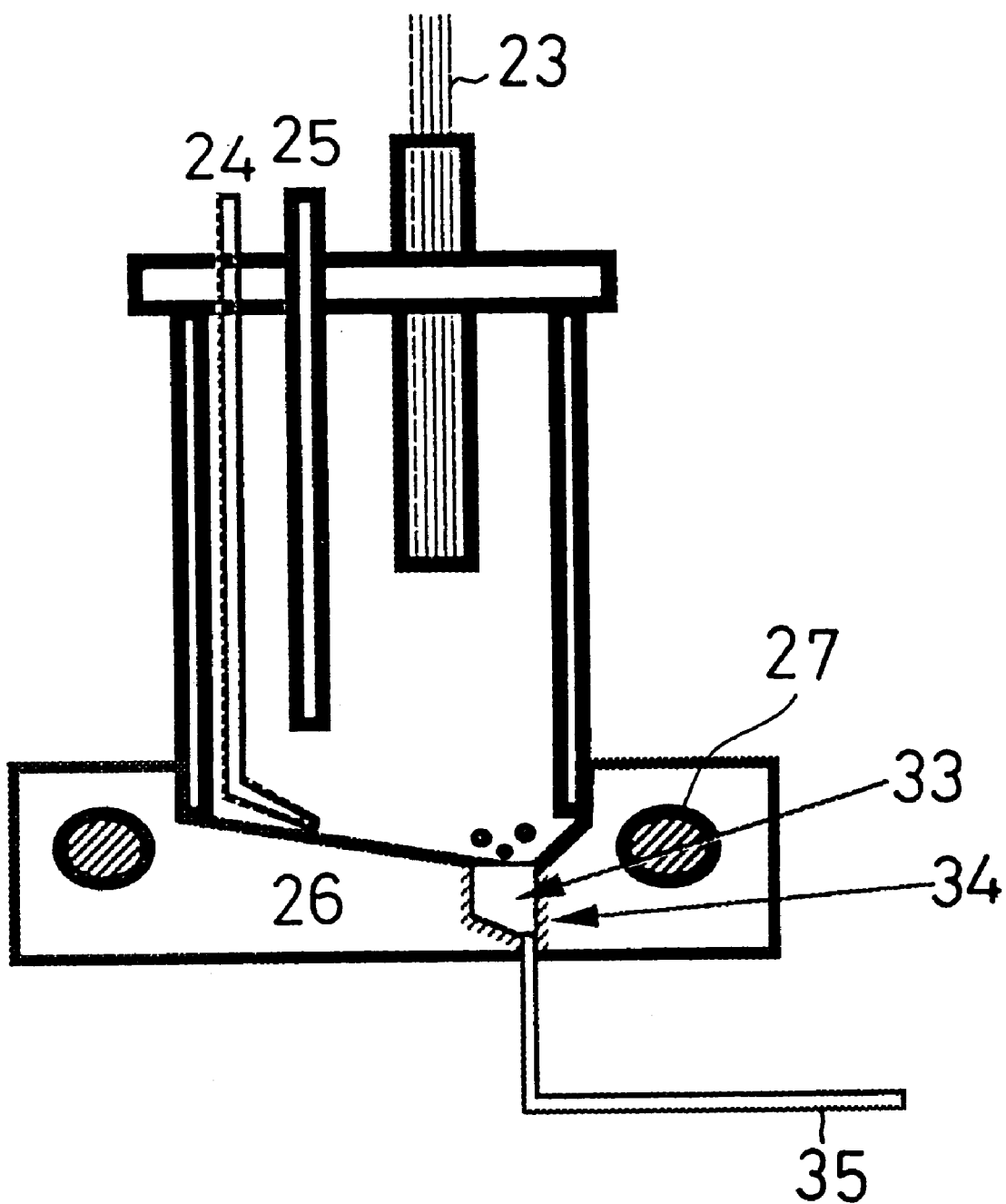
FIG. 13 is a view for describing a concentrated sample take-out unit of the concentrating apparatus of the Fourth Preferred Embodiment according to the present invention.

In this apparatus, the construction of a take-out opening in the container bottom 21 which makes it easier to control the concentrating rate of the concentrated liquid is illustrated in FIG. 13. The eluent vaporized mainly on the heated metallic surface of the container bottom, and moves into the gas phase. Accordingly, in the bottom of the container, there is disposed a chamber (approx. 0.5 ml) 33 whose volume corresponds to the amount of the concentrated liquid which is expected to secure. The surface of the chamber is made into a Teflon coat 34 layer. And, from the bottom, there is disposed a take-out opening 35. Since the surface of the chamber 33 is coated with a material of low thermal conductivity which is different from the metal, the vaporization speed of the concentration liquid is slowed down in the chamber so that it is easy to control the concentration magnification. Therefore, it is possible to obtain a solution of constant concentration rate as a sample for analysis. The solution, which is concentrated by a constant concentrating rate, can be transferred as a sample for the NMR analysis as it is.

Note that the aforementioned volume-varying means is not limited to the combination of the piston and cylinder illustrated in FIG. 12. For instance, there is a method in which an appropriate number of capillaries (one in which a couple of capillaries are bundled to fine adjustment, one in which dozens of capillaries are bundled to rough adjustment, or one in which all capillaries are divided into an equal number and are bundled together, etc.) can be connected with a metallic container provided with a valve, and in which the capillaries can be closed by the valve. Alternatively, there is a method in which all capillaries are accommodated in a single container, and in which a couple of the capillaries can be closed by a rotary-type valve. Note that, in the case of this preferred embodiment, it is characterized in that the adjustment can be carried out for each of the capillaries over the region of the entire number of the capillaries.

Note that the heavy-hydrogenated solvents which are used in an LC/NMR are generally expensive. After the solvent, which has been evacuated from the volume-varying means, is recovered, it can be reused by refining with a silica gel column, etc. Moreover, it is possible to inhibit the contamination of the working environment which results from the vaporization of the solvent to the outside of the system.

Fifth Preferred Embodiment

Figure 14:
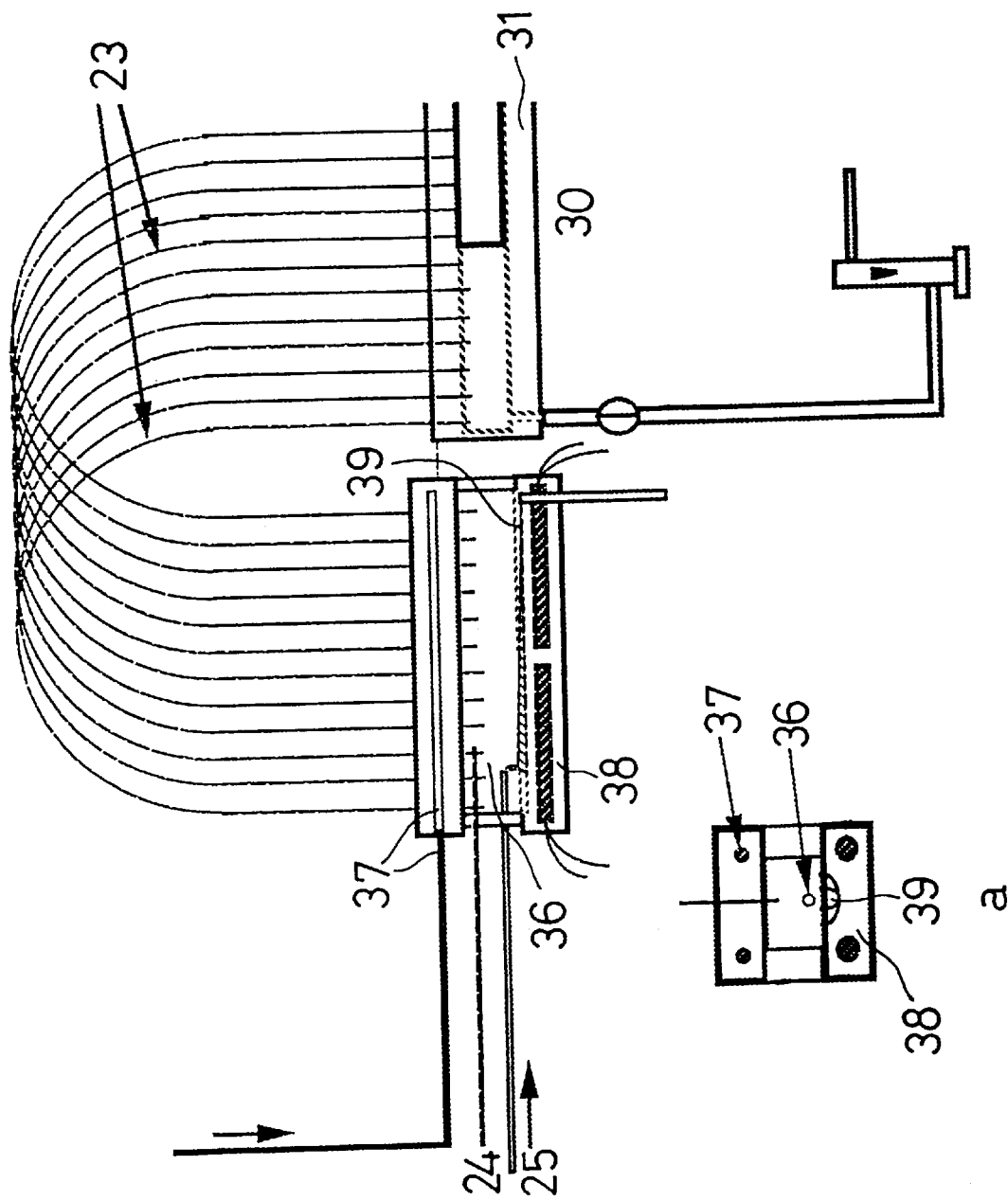
FIG. 14 is a view of a concentrating apparatus of a Fifth Preferred Embodiment according to the present invention; wherein FIG. "a" is a side cross-section view of the concentrating apparatus.

As illustrated in FIG. 14, a container which concentrates a solution coming from an HPLC is a rectangular container 36 whose cross-section is a square. In the upper surface or the side surface of the container 36, a large number of capillaries 23 are attached linearly in a line or in a plurality of lines. And, a water-cooling pipe 37 for cooling the periphery of the capillaries 23 is buried. Whilst, in the bottom inner surface 38 of a heating container, as illustrated in the side cross-sectional view of FIG. 14a, there is disposed a passage 39 for guiding an HPLC eluent. In the same bottom surface 38, there is buried a cartridge heater so that the bottom surface 38 can be heated. After the eluent coming from the HPLC or GPC is introduced into this container 36, it is poured into the aforementioned passage 39. The poured solution is put into a dried state shortly, and does not flow at all. Accordingly, in this preferred embodiment, in order to secure the fluidity of the solution and to make the concentrating rate of the solution transferred to the NMR to be a predetermined value (for example, the concentration of the flowing-in solution is 1%, the concentration of the flowing-out solution if 10%, namely the concentrating rate: 10 times), the properties can be adjusted by using the volume-varying means 30.

As concrete means, the same volume-varying means 30 as used in FIG. 12 is used, and the position of the piston was moved in accordance with the amount of the solvent evacuated from the container 31 to adjust the concentration speed. Namely, in the case that the elute coming from the HPLC loses the fluidity before it reaches the right end, the insertion distance of the piston on the right side of FIG. 14 is increased, and thereby the outlets of a large number of the capillaries 23 are closed. In the opposite case, the piston is adjusted so as to open the outlets of the capillaries 23 in a large number. Note that, similarly to the Fourth Preferred Embodiment, the concentrating rate is obtained by the flow rate of the HPLC and the flow rate of the solvent discharged from the container 30.

Note that the airtightness between the pipe for introducing the HPLC solution and the side surface of the concentration container is maintained by, for example, an O-ring which is made of a perfluororubber.

Sixth Preferred Embodiment

Figure 15:
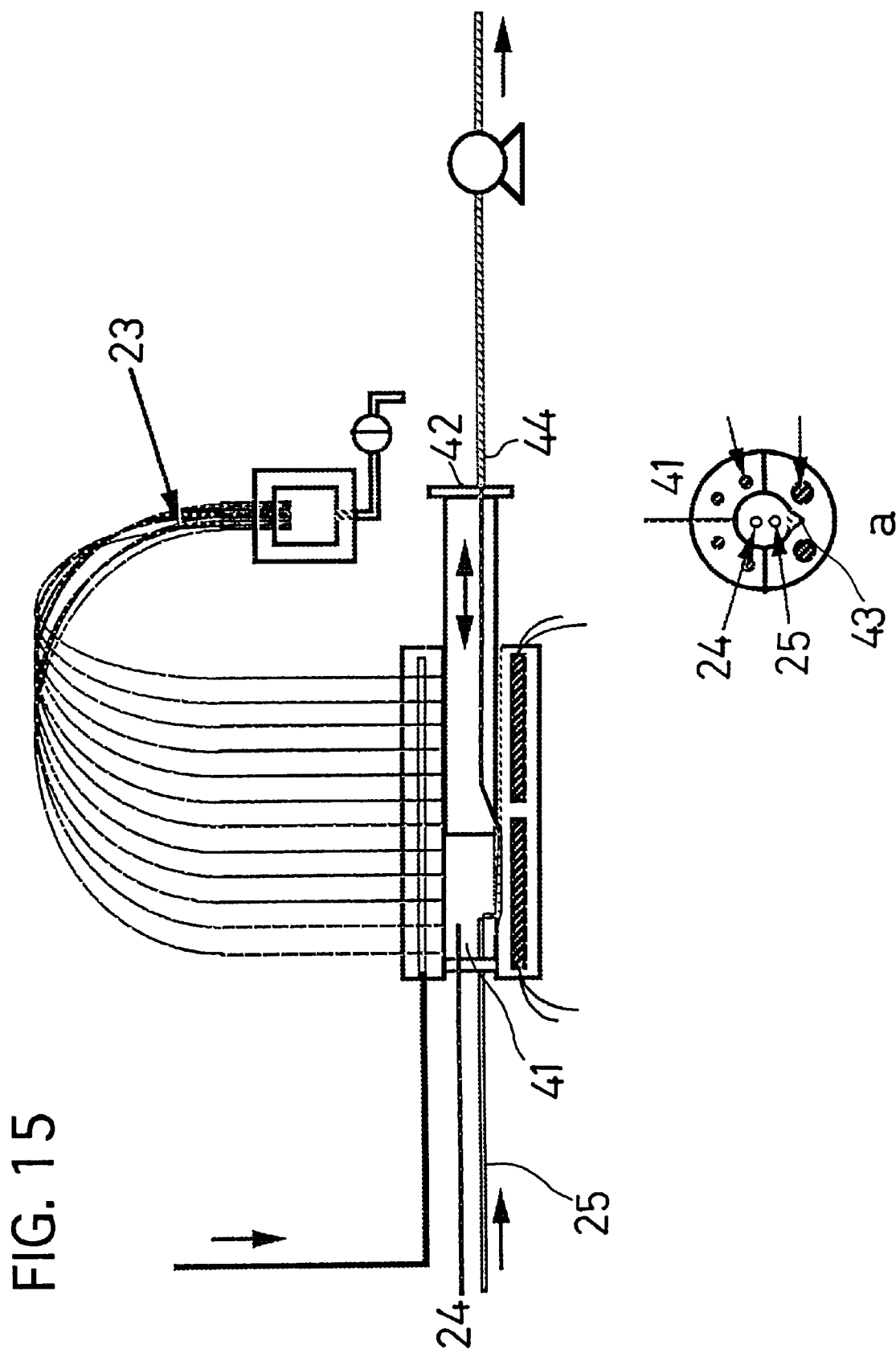
FIG. 15 is a view of a concentrating apparatus of a Sixth Preferred Embodiment according to the present invention; wherein FIG. "a" is a side cross-section view of the concentrating apparatus.

An apparatus used in the Sixth Preferred Embodiment integrates the solution-heating-side container and the volume-varying means. Its solution-heating chamber is illustrated in FIG. 15, and its side-wise cross-sectional view is illustrated in FIG. 15a. In the upper surface of a fine and long cylinder-shaped cylinder 41, there is attached capillaries 23 for discharging a solvent. In the inside bottom surface of the cylinder 41, excepting the opposite ends, there is formed a solvent passage. Into the cylinder 41, there is a piston 42 which is snugly fitted with the cylinder 41 is inserted. Namely, on the lower surface of the piston 42, there is disposed a projection which corresponds to a groove in the bottom of the cylinder 41. The solution coming from the HPLC and introduced into the cylinder 41 by way of a pipe 25 is concentrated while it flows in the groove 43. And, it is dammed up by the piston 42 which has the projection on the lower surface. The dammed-up solution is then entered into a hole which is disposed under the piston 42, and passes through the passage 44 of the piston. Thereafter, the solution is sucked out by a suction pump, and is introduced into the NMR, an analyzing apparatus.

Seventh Preferred Embodiment

In the case that an HPLC solution is subjected to an IR measurement, it is necessary to completely concentrate the solution. In a system in which an LC and the other analyzing apparatus are combined, and in the case that the analyzing apparatus is of low sensitivity, or in the case that the concentration of the solution is low, the Stopped-Flow is carried out in which the measurement is done while stopping the moving phase of the HPLC. However, in the Stopped-Flow, the solutes diffuse in the passages of the HPLC and the interface, and accordingly there arises a problem in that the separating capacity degrades. Therefore, it is desired to carry out the measurement in the On-Flow.

In the case that the solution-concentrating chamber used in the Fourth Preferred Embodiment is used, it is impossible to completely concentrate the solution while introducing the solution from the HPLC. Accordingly, in a Seventh Preferred Embodiment and an Eighth Preferred Embodiment, in addition to a chamber for semi-concentrating the solution coming from the HPLC, another chamber is disposed to completely concentrate the solution. And, these are heated at the temperature of the boiling point of the solvent.

Figure 16:
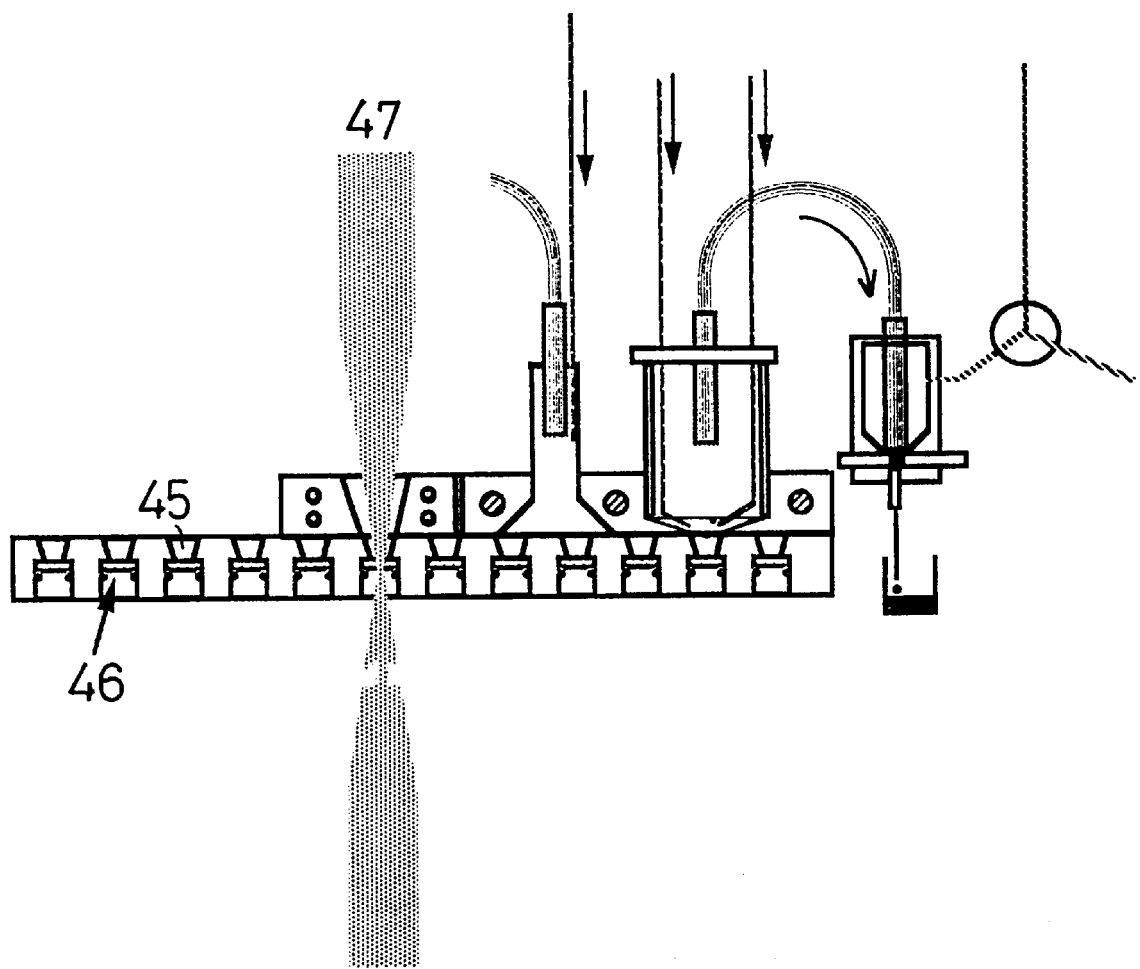
FIG. 16 is a view of a concentrating apparatus of a Seventh Preferred Embodiment including a take-out unit, and cells for an infrared analysis synchronizing with the take-out unit.

For example, as illustrated in FIG. 16, in a guide of a rectangular parallelepiped, there is accommodated a solution coming from an HPLC, and there is disposed a concentration cell 45 (a dent whose side-wise cross-section is a trapezoid shape and which enables a beam 47 of an infrared system to transmit is disposed. And, the trapezoid-shaped bottom surface 46 is provided with an aperture which is formed of a material transparent to infrared rays, for instance, KBr.) for providing a concentration field. A plurality of such concentration cells 45 are disposed. The upper surface of the aforementioned rectangular-parallelepiped-shaped guide 45 is finished to a flat mirror surface. And, the mirror surface and the lower surface of (or the hole of) the semi-concentrating container or the lower surface of (or the hole of) the completely-concentrating container are pressed and brought into contact with each other by way of an O-ring which is made of a perfluororubber. The solutes completely concentrated in the completely-concentrating container is then cooled by a metallic block which is water-cooled, are thereafter passed through a semi-airtight room, which has been purged by a He gas, etc., and are thereby subjected to an infrared analysis. After the measurement, the sample stage is removed, and is washed after the solutes in the fraction cells are recovered.

Eighth Preferred Embodiment

Figure 17:
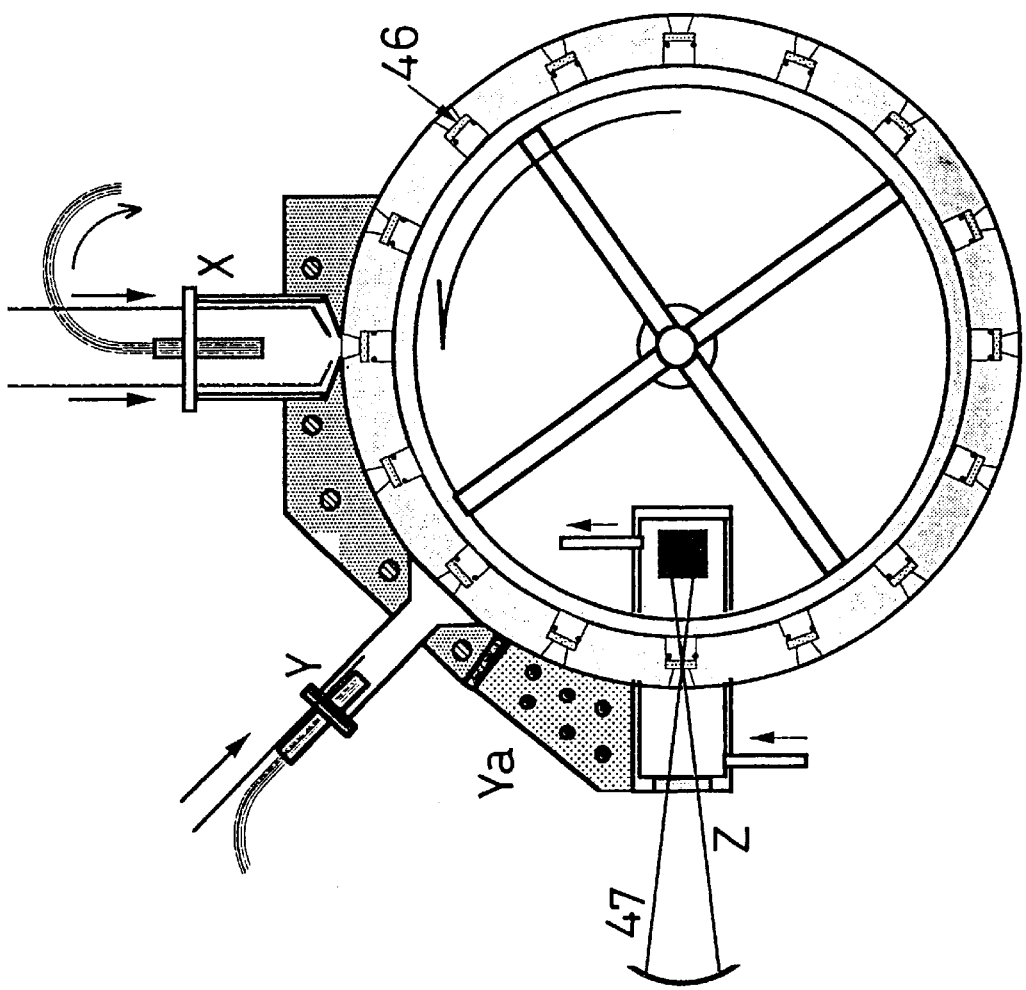
FIG. 17 is a view concentrating apparatus of an Eighth Preferred Embodiment including a take-out unit and cells for an infrared analysis synchronizing with the take-out unit.

In the Seventh Preferred Embodiment, when all of the infrared analysis cells 45, disposed in the sample stage, are used, the analysis should be interrupted. Accordingly, as illustrated in FIG. 17, an apparatus was manufactured in which fraction cells are attached in a disk-shaped manner so that an LC/IR measurement can be carried out endlessly. In this preferred embodiment, a solution coming from an HPLC is processed in the following order: it is semi-concentrated at "X", is completely concentrated at "Y", is cooled at "Ya", and is subjected to the IR measurement at "Z". Thereafter, the fraction cells are washed at around immediately below the semi-concentration chamber, are dried, and used for the next concentration.

Ninth Preferred Embodiment

Figure 18:
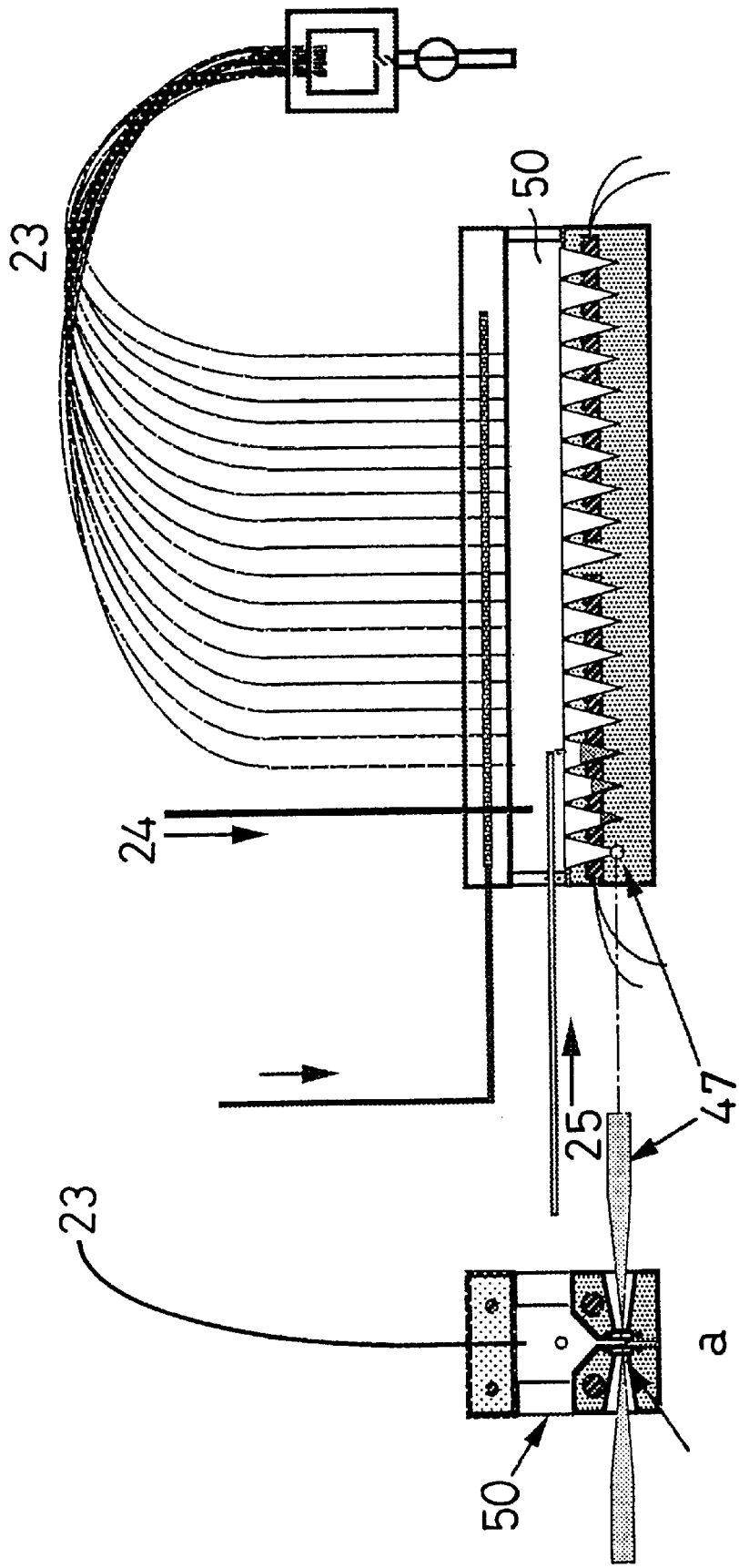
FIG. 18 is a view of a concentrating apparatus of a Ninth Preferred Embodiment including a take-out unit, and cells for an infrared analysis synchronizing with the take-out unit.

In the Seventh Preferred Embodiment and the Eighth Preferred Embodiment, the samples are subjected to the IR measurement in the semi-airtight cells 45 after they were cooled. In the Seventh and Eighth Preferred Embodiments, since the cells 45 are not airtight completely, there remains a possibility of losing substances which are likely to vaporize. Accordingly, in the Ninth Preferred Embodiment, the semi-concentration of the solution, the complete concentration and the IR measurement are carried out in an identical air-proof chamber 50 as illustrated in FIGS. 18 and 18a of the side-wide cross-section of a cell. One which connects this chamber with the outside is capillaries only. Therefore, except a solute whose boiling point is close to that of a solvent, the solute is hardly lost. In this Preferred Embodiment, the pitches of the dents, which are seen in the cross-section for receiving fractions in the chamber 50, relate to the separating capacity of the LC/IR. Then, the required number of the capillaries mainly depends on the flowing-in speed 25 of the solution coming from the HPLC, the flowing rate of the bubbling gas 24 and the chamber temperature. In the LC/IR, a sufficient number of capillaries are connected so that the complete concentration is achieved.

Tenth Preferred Embodiment

This preferred embodiment is a method for recovering a concentrated solution.

Figure 10:
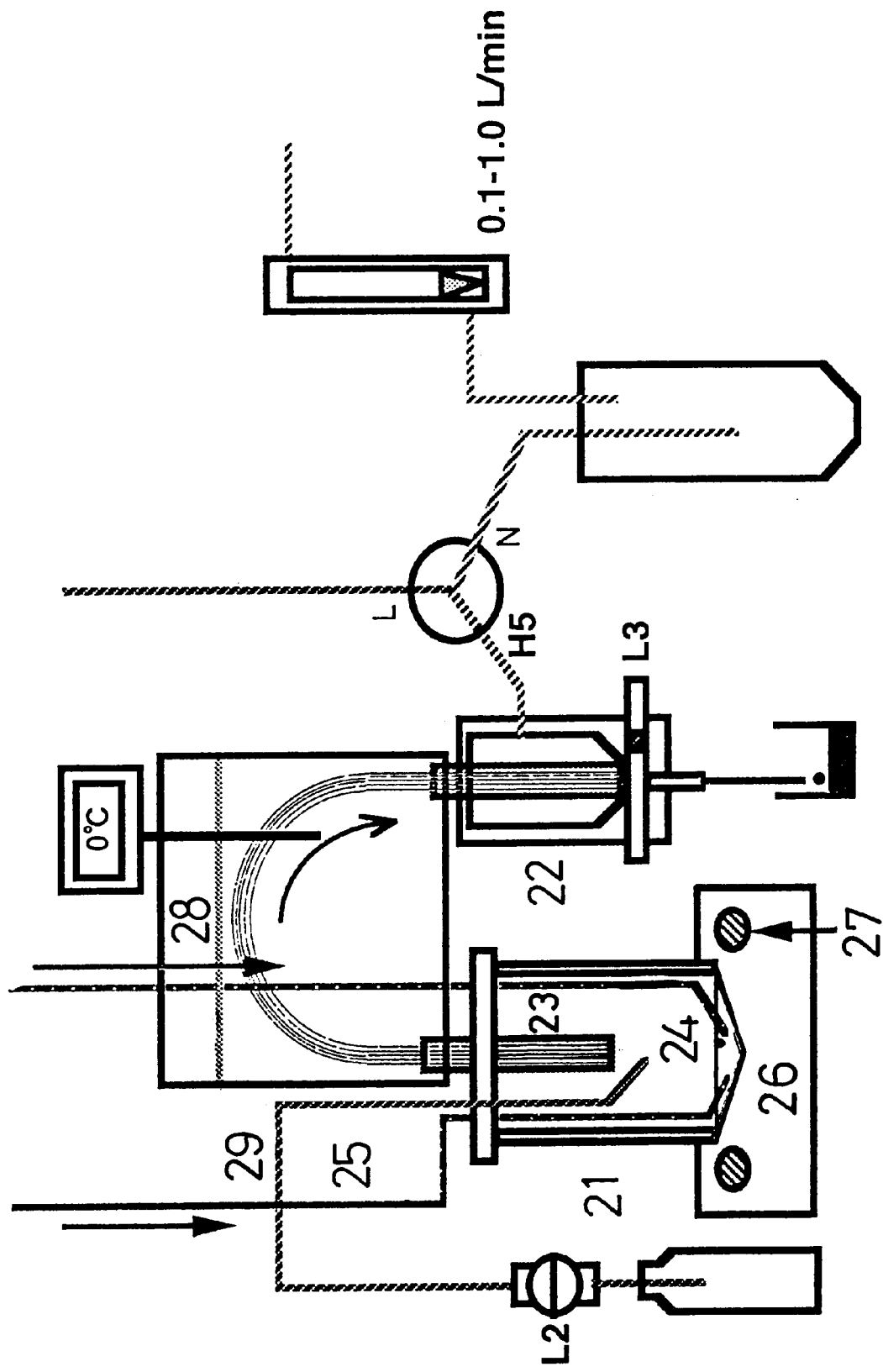
FIG. 10 is an explanatory diagram of another concentrating apparatus according to the present invention.
Figure 11:
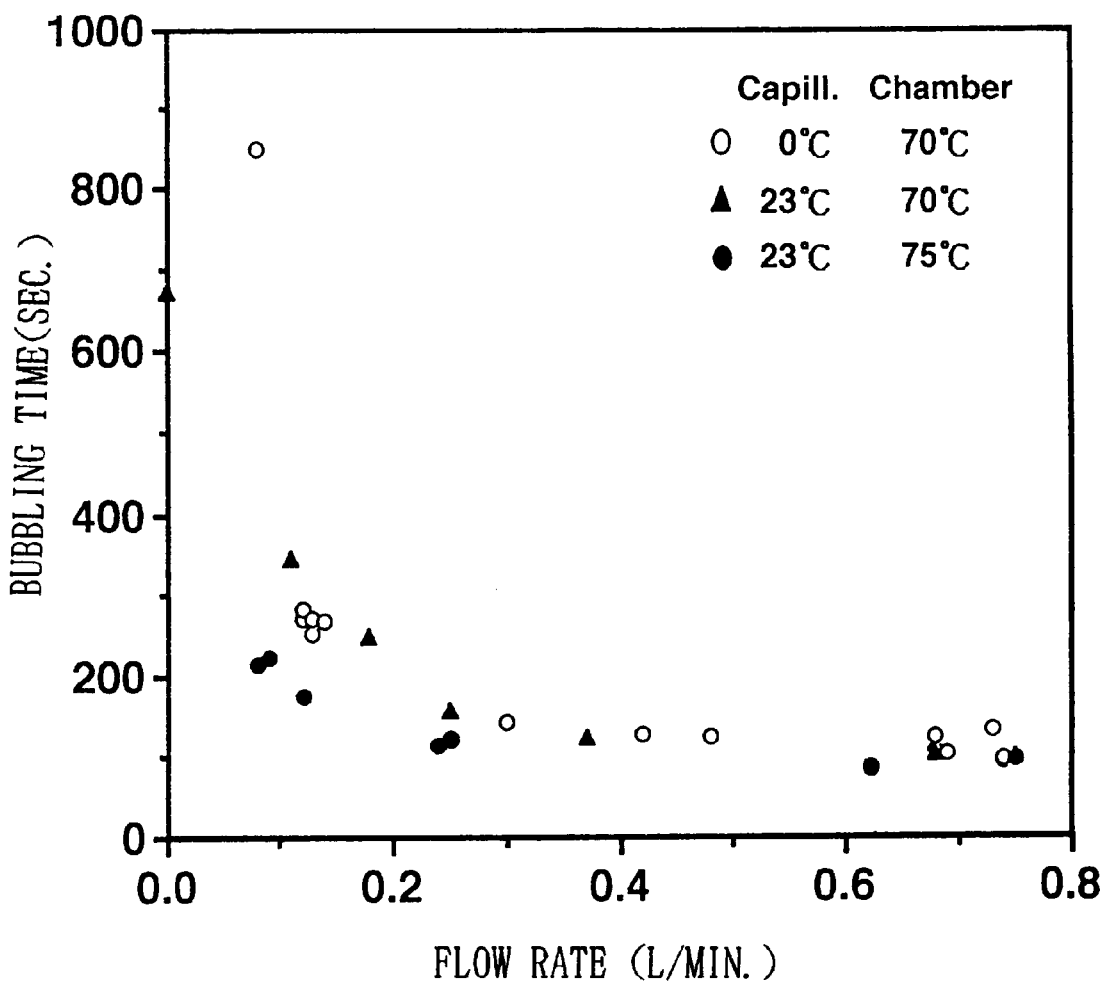
FIG. 11 is a graph for illustrating the relationship between He flow rate and bubbling time.
Figure 19:
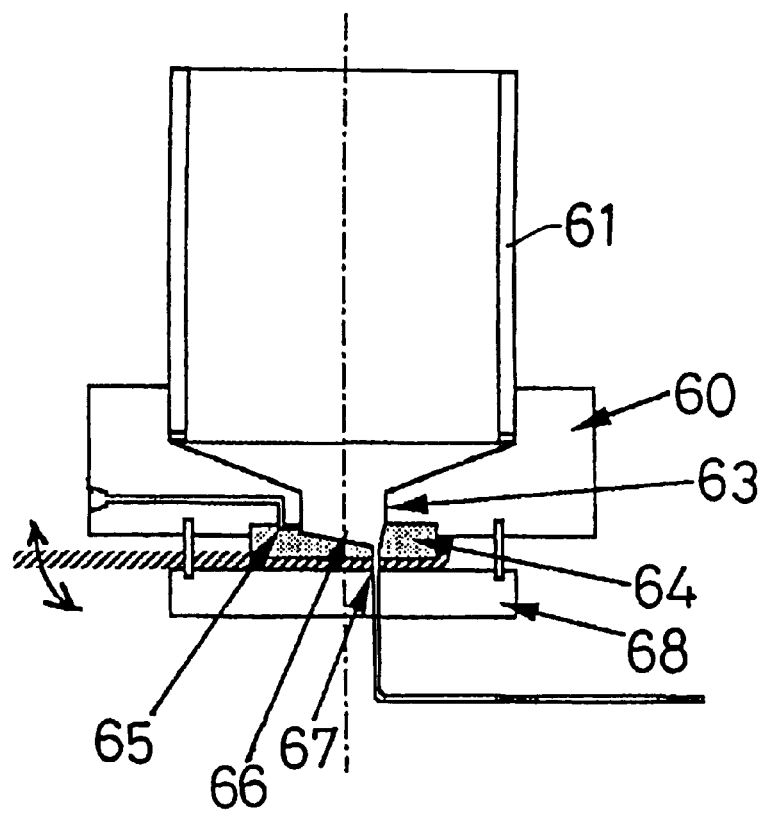
FIG. 19 is an explanatory diagram of a concentration-and-recovery switching valve provided for a concentrating apparatus of a Tenth Preferred Embodiment according to the present invention.
Figure 20:
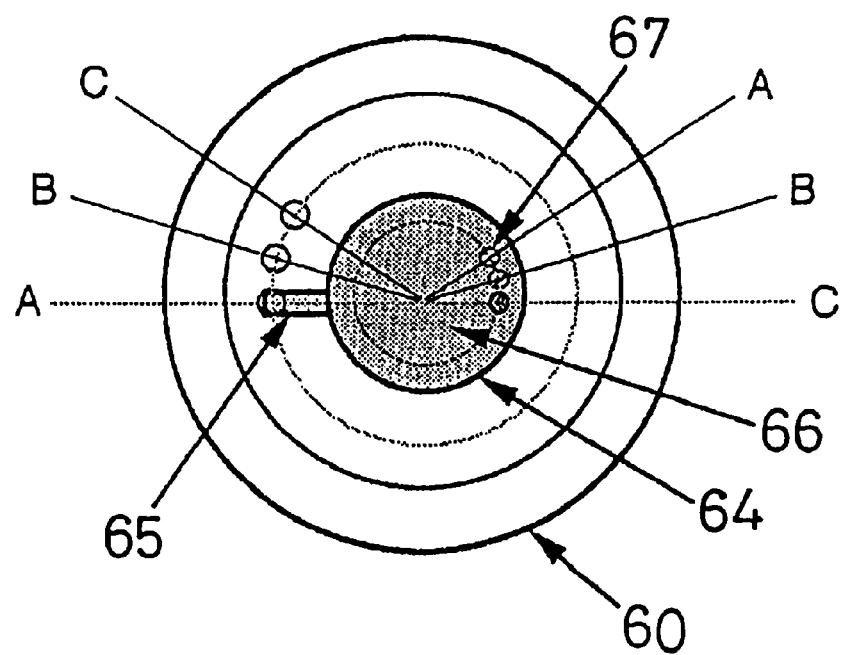
FIG. 20 is a plan view of the recovery switching valve of FIG. 19.

In the concentration chambers above which all the pipes are placed above as shown in FIGS. 10 and 13, it is necessary to ascend and descend the pipes. Thus, the operation is cumbersome. Accordingly, a valve is used whose side-wise cross-sectional view is illustrated in FIG. 19, and whose plan view is illustrated in FIG. 20.

This valve is constituted by a block 60 for heating a solution, a valve rotor 64, and a supporting plate 68 for pressing the valve rotor 64 onto the heating block 60. The block 60 has a cone-shaped dent for collecting the concentrated liquid in the center of the concentration chamber and a cylinder-shaped hole 63 for guiding the concentrated liquid to the valve rotor 64. The valve rotor 64 is provided with a groove 65 for introducing a bubbling gas to a concentration stage. As illustrated in FIG. 20, the groove 65 is placed so that it meets an outlet of a bubbling-gas supplying pipe which is built in the heating block. The concentrated-liquid recovering hole and the concentrated-liquid recovering pipe 67 are placed so that they are connected. As illustrated in FIG. 20, the groove 65 and the concentrated-liquid recovering hole are placed at the position of about 135 degrees, for example, with respect to the center of a circle. In FIG. 20, when the valve rotor 64 is at the position of "A", the bubbling gas is supplied. When the valve rotor 64 is at "C", the concentrate or the concentrated liquid is recovered. The position of "B" is a neutral state, and all of the holes are closed.

By using this valve, the concentration operation could be simplified. Moreover, by introducing this valve, the concentration could be automated with ease.

By the way, in the case that a concentrate is recovered with a small amount of a solvent, there arises a problem in that the solvent, which is poured in the container 61 through the capillaries, is heated at the bottom of the concentration chamber 66 and a part thereof is vaporized. In the valve illustrated in FIG. 20, the valve rotor 4 is made from Teflon of low thermal conductivity. This is selected mainly considering the metallic surface of the mating member and the sealing property. As a one extra effect, decreasing the concentration speed is expected. Namely, when the liquid surface of the concentrated liquid is at the height of the upper end of this rotor or less, the concentration speed slows down. Consequently, it is easy to control the amount of the concentrated liquid (liquid-surface height). Moreover, the vaporization of a recovery solvent, which is poured from the upper side after the concentration, can be suppressed. Namely, the solvent, which is poured for recovery, can be recovered without a loss.

Eleventh Preferred Embodiment

Figure 21:
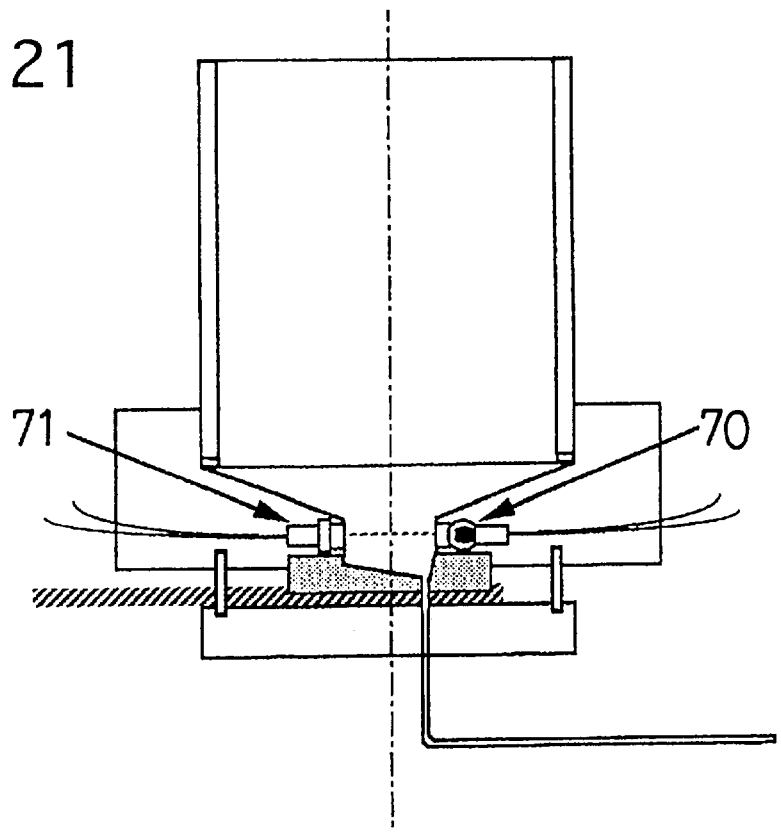
FIG. 21 is a view of an apparatus for detecting a concentrated liquid level by a photoelectric system, the apparatus provided for a concentration container.

Three methods can be contemplated as a method for detecting the amount of the concentrated liquid (liquid-surface height). A first method is, as illustrated in FIG. 21, a method in which a photo source 70 and a photoelectric cell 71 are placed at a peripheral portion of a hole of a heating stage where a concentrated liquid is collected to carry out the detection.

Figure 22:
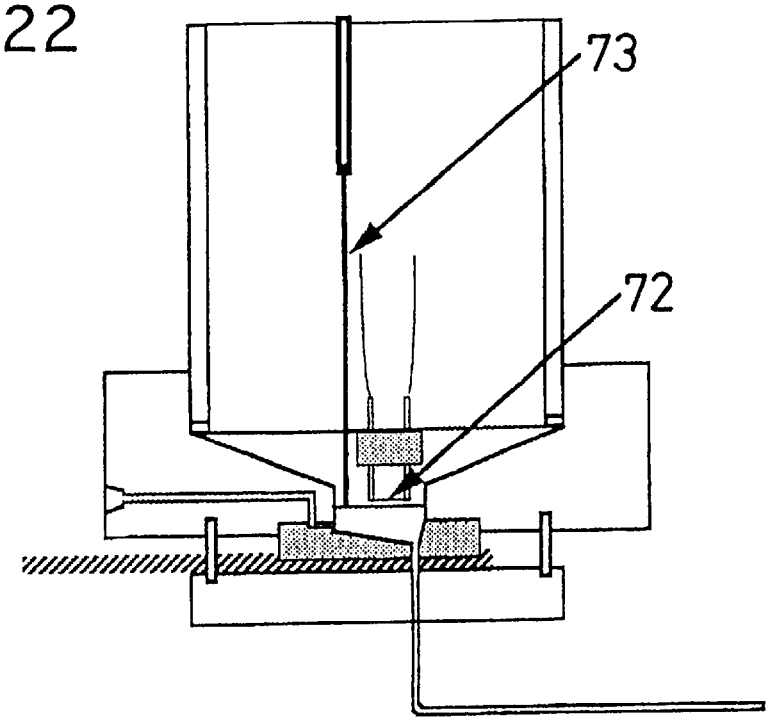
FIG. 22 is a view of a mechanism for detecting a concentrated liquid level by a resistance detector and a thermocouple, the mechanism provided for a concentration container.

A second method is, as illustrated in FIG. 22, a method in which a resistance wire 72 of high thermal resistance coefficient is spanned between the heads of two pillars to incorporate it into a bridge circuit to carry out the detection. Since there is a possibility of igniting the solvent by heating the resistance wire, this method is not preferable excepting for water-based solvents.

A third method is, as illustrated in FIG. 22, a method in which a thermocouple of low heat capacity 73 is inserted from the upper side and the leading end is set at a predetermined liquid surface to carry out the detection.

Twelfth Preferred Embodiment

When recovering a concentrate with a trace amount (for example, on the order of 100 $\mu$L), the amount of the solvent, which is vaporized by the heat of the heating stage, should not be neglected. Accordingly, in order to make the vaporization of the solvent poured to recover the concentrate minimum, two methods were investigated.

Figure 23:
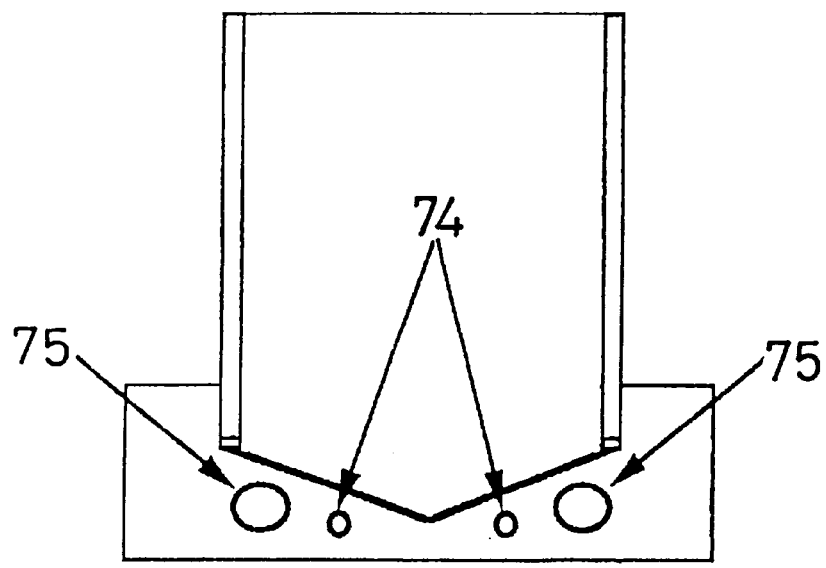
FIG. 23 is an explanatory view of a cooling apparatus for recovering by a solvent of a trace amount, the cooling apparatus provided for a concentration container.
Figure 24:
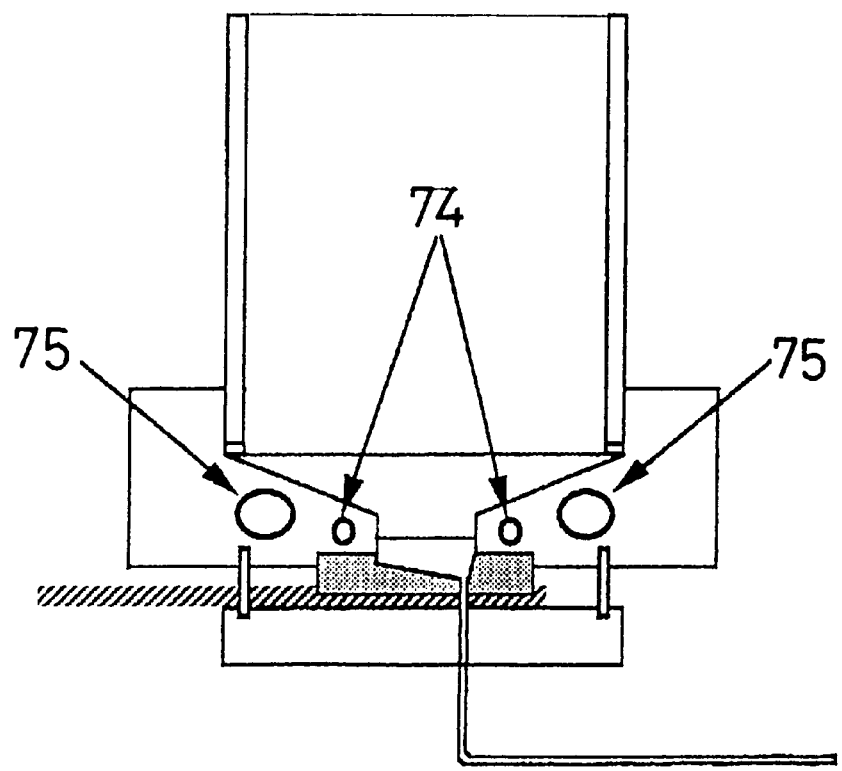
FIG. 24 is an explanatory view how a take-out unit for recovering by a solvent of a trace amount is cooled, the take-out unit provided for a concentration container.

The first one of them is, as illustrated in FIG. 23 and FIG. 24, a method in which cooling water 74 is flowed adjacent to the center where the concentrate gathers. After the concentration is finished, the electric power source of a heater 75 of a block is turned off, and cooling water is flowed. And, when the temperature of the heating stage is 40° C. approximately, a small amount of a solvent is poured, and a concentrated solution is obtained which is made into a solution with an as-intended amount of the solvent.

The second method is, as illustrated in FIG. 24, a method in which a dent, which is covered with a material of low thermal conductivity and has a predetermined volume, is disposed in the inner wall of a bottom 25 of the heating stage. The solvent poured in the dent is not heated directly, and hardly vaporizes. Namely, most of the poured solvent is recovered as a solution.

Thirteenth Preferred Embodiment

Concentrating Apparatus Utilizing Porous Filter

Figure 25:
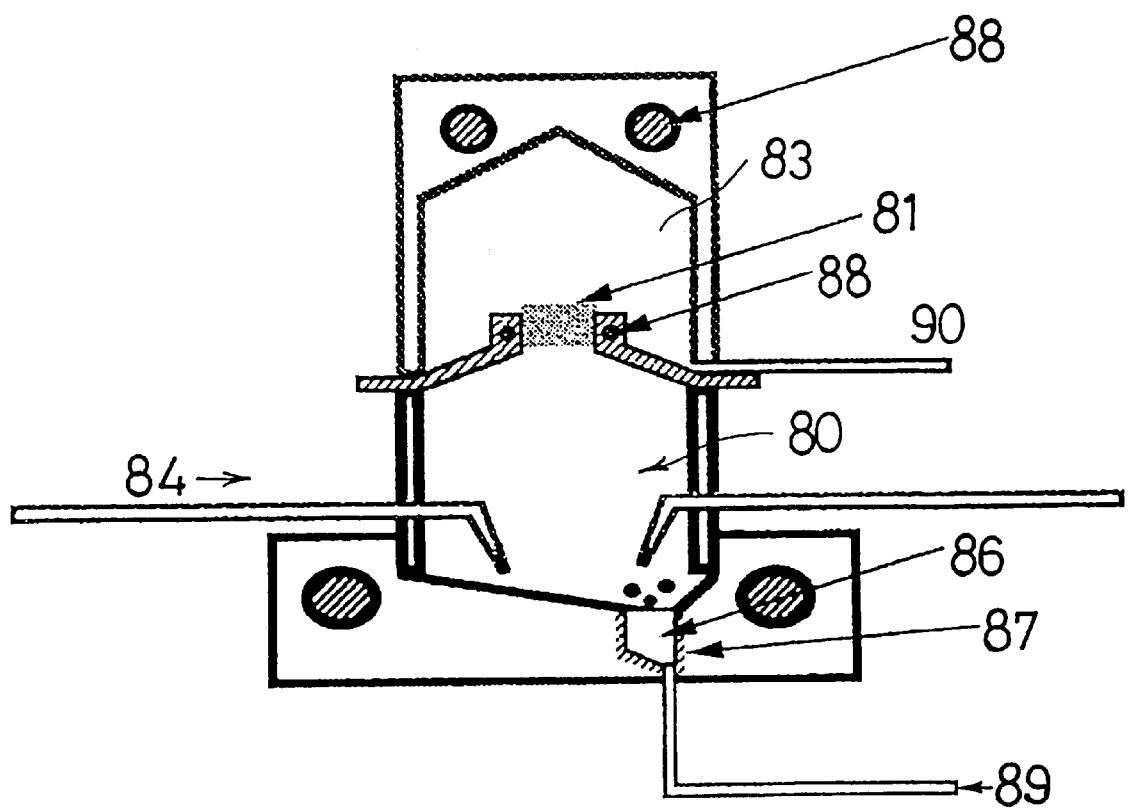
FIG. 25 is a rough explanatory diagram of a concentrating apparatus utilizing a porous filter of a Thirteenth Preferred Embodiment according to the present invention.

The outline of this apparatus is illustrated in FIG. 25. In a ceiling portion of a concentration container 80, there is disposed a porous filter 81 whose pore size is 0.5 mm or less. The inner surface of this filter is coated with a chemical (for example, non-polar polydimethylsiloxane, or polar polyethylene glycol) which exhibits appropriate non-polarity. When the one coated with a non-polar chemical is used, it can be used to concentrate a solution which contains solutes whose boiling points are close to that of a solvent. When the one coated with a polar chemical is used, it can be used to concentrate a solution which contains solutes whose boiling points are adjacent to that of a solvent, and which exhibits high polarity.

An HPLC eluent which is introduced into the container 80 is heated while it is subjected to bubbling by an inert gas, e.g., helium. The vaporized solvent is passed in the porous filter 81 and entered into an upper chamber 83 by the inert gas 84. And, it is cooled at the ceiling portion which is cooled by cooling water 88, and is collected together with the inert gas through a recovery opening 90, which is disposed in the side surface. The solutes are captured at the lower portion of the filter, and is collected by back flushing, etc., in an take-out opening 86 which is placed in the bottom surface of the container, and which is coated with a resin 87. And, they are recovered through a pipe 89. In the side surface of the filter 81, there is flowed the cooling water 88 whose temperature is controlled. And, during the concentration, the filter is cooled so that the capturing efficiency of low-boiling-point substances is enhanced. In the recovery of the substances captured in the filter, the temperature is increased so as to make the desorption easy.

In accordance with the method of the present invention, it is possible to remove only the solvent from the dilute solution, which is obtained by the first liquid chromatography, without a loss of the low-boiling-point substances. And, the total amount (without losing) of the elutes of the first column, except the solvent, is made into a solution with the solvent of the second liquid chromatography, and is supplied as a sample for the second liquid chromatography. Therefore, a response is obtained which corresponds to the amount of the sample which is supplied to the first liquid chromatography.

Among the concentrated solutes, the components which are insoluble to the solvent used in the second liquid chromatography can be removed by a filter which is disposed downstream to the piping 89.

Note that, in accordance with the concentrating apparatus of the present invention, not limited to the HPLC described so far, a sample which contains a substance whose boiling point is slightly higher than that of a solvent can be separated with apparatuses (for example, the gel permeation chromatography, the super critical fluid chromatography, etc.) which carry out the separation with solvents of relatively low boiling points, and can be analyzed in a real time. Moreover, since all of the solvent, which is separated by the concentration operation, can be recovered, it is especially advantageous when toxic solvents or high-cost solvents are used.

In addition, since the solution coming from the HPLC, SFC or GPC can be introduced into the NMR while concentrating it on-line, it is possible to carry out the On-Flow measurement which has been difficult to carry out conventionally. Regarding the LC/IR, which has been carried out conventionally with solvents which adsorb the infrared radiation less (the types of the solvents are limited), the measurement can be carried out without being interrupted by the solvents at all. In the LC/IR or GPC/IR which has been carried out in the open system, it is possible to carry out the measurement without a loss on the concentration operation.

By disposing a chamber whose surface is coated with Teflon in the bottom of the concentration container, it is possible to lower the concentration speed and accordingly to easily control the concentrating rate.

Here, the difference between the conventional gas chromatography and the concentration method of the present invention will be described in terms of the operation mechanism. In the conventional gas chromatography, all of the substances constituting the solution are injected into the capillary column along with the carrier gas (gas phase). The substances injected into the column contacts with the surface of the liquid phase which is coated on the inner wall of the column. Substances whose boiling points are high or substances which exhibit high solubility with the liquid phase are present in the liquid-phase area in a long time, and moves at low speed into the gas phase. Whilst, substances whose boiling points are low move at high speed from the liquid phase to the gas phase, and accordingly are present in the gas phase in a long time. As a result, they pass fast through the column.

For instance, in the column whose inner wall is coated with non-polar polydimethylsiloxane, the substances whose boiling points are low mainly pass through the column faster than the other substances. Moreover, when the substances whose boiling points are identical with each other exist, one of the substances whose polarity is lower passes faster than the other substances.

On the other hand, in the present process for concentrating a solution according to the present invention, among the substances constituting the solution, only a substance which is expected to be separated from the solution is introduced into the capillary. For example, when only the solvent is expected to be removed, the bubbling is carried out at the temperature at which only the solvent vaporizes so that only the solvent is fed into the capillary. When the solvent is n-hexane, the temperature of the capillary is kept at room temperature. At room temperature, the liquid film (polydimethylsiloxane) coated on the inner surface of the capillary exhibits a low ability to retain the n-hexane. Moreover, since the n-hexane has a low boiling point, most of it is present in the gas phase, and moves along with the carrier gas. Whilst, since the hydrocarbons, which are vaporized by heating together with the n-hexane and whose number of carbon atoms are 8–9, have higher boiling points than that of the n-hexane, they are likely to remain in the liquid phase. Consequently, they are concentrated in the inside or the surface of the liquid film on the inlet of the capillary. And, there arises an inverse concentration gradient with respect to the hydrocarbons whose number of carbon atoms is 8 and 9, and which are present in the upstream-side gas phase in the inlet of the capillary so that the intrusion is inhibited.

For example, when a solute whose boiling point is lower than that of a solvent is expected to be taken out, the bubbling is carried out at the temperature at which only the solute vaporizes, and only the solute is fed into the capillary. In this case, the temperature of the capillary is decreased to such a temperature that the n-hexane cannot pass through. And, by carrying out the bubbling, the n-hexane, which vaporizes along with the low-boiling-point solute, is trapped at the inlet of the capillary. Thus, with the concentration gradient (inverse gradient) of the n-hexane, the intrusion of the n-hexane can be inhibited. Hence, only the low-boiling-point solute can be transferred in the capillary.

INDUSTRIAL APPLICABILITY

The method for concentrating a solution according to the present invention, and the apparatus for the same can concentrate a solution containing a solute whose boiling point is close to the boiling point of a solvent or a solution containing a solute whose polarity differs from the polarity of a solvent without a loss of the solute. The resulting concentrate can be used as a sample for the subsequently applied analyzing means. Thus, they are useful in making the analysis on trace-amount components efficient, and in upgrading the accuracy of the analysis.

What is claimed is:

1. A method for separating a solute from a solvent and concentrating a solution, comprising the steps of:
   vaporizing at least one of the solvent and the solute;
   selectively adsorbing at least one of the vaporized solvent and the solute on an adsorbent which has an ability to selectively adsorb on of the solvent and the solute;
   thereby selectively separating the solvent and the solute; and increasing the concentration of the solute in the solution;
   wherein the boiling points or the polarities of said solute and said solvent are different from each other.

2. The method according to claim 1, wherein the adsorbent is selected from the group consisting of a capillary, an assemble of capillaries, a tube packed with diatomaceous earth or polymer, and a porous filter.

3. The method according to claim 2, wherein the capillary or the assemble of capillaries has an inner diameter in the range of from 0.1 mm to 1.0 mm.

4. The method according to claim 2, wherein said capillary, said assemble of capillaries or said porous filter is coated with polar or non-polar chemicals or an inner wall thereof.

5. The method according to claim 2, wherein a surface of the diatomaceous earth or the polymer in the packed tube is coated with polar or non-polar chemicals.

6. The method according to claim 1, wherein the vaporizing is carried out by heating.

7. The method according to claim 6, wherein the heating is carried out at a temperature near a boiling point of the vaporized solvent or the solute.

8. The method according to claim 1, wherein the vaporizing is carried out with a carrier gas.

9. The method according to claim 1, wherein the adsorbent is connected to a volume-varying device for controlling a transfer amount of the vaporized solvent and solute.

10. The method according to claim 9, wherein the volume-varying device has one opening at the end of the adsorbent.

11. The method according to claim 1, wherein said solvent is a hydrophobic solvent.

12. The method according to claim 1, wherein said solvent is a hydrocarbon solvent.

13. The method according to claim 1, further comprising transferring the concentrated solution to an analytical device.

14. The method according to claim 13, wherein the analytical device is an IR, NMR, or MS.

15. The method according to claim 1, wherein at least one of the solvent and the solute with a higher boiling point or a higher polarity is adsorbed on said adsorbent.

16. A device for separating a solute from a solvent and concentrating a solution, comprising:
   a vessel for containing a solute and a solvent;
   an adsorbent having a selective adsorbing ability and having an opening which is opened in the vessel;
   wherein at least one of the solvent and the solute is vaporized in said vessel; and
   wherein at least one of the solvent and the solute is transferred through the adsorbent.

17. The device according to claim 16, wherein the adsorbent is selected from the group consisting of a capillary, an assemble of capillaries, a tube packed with diatomaceous earth or polymer, and a porous filter.

18. The device according to claim 17, wherein said capillary, said assemble of capillaries, or said porous filter is coated with polar or non-polar chemicals on an inner wall thereof.

19. The device according to claim 17, wherein a surface of the diatomaceous earth or the polymer in the packed tube is coated with polar or non-polar chemicals.

20. The device according to claim 17, wherein the capillary or the assemble of capillaries has an inner diameter in the range of from 0.1 mm to 1.0 mm.

21. The device according to claim 16, wherein the adsorbent is connected to a volume-varying device for controlling a transfer amount of the vaporized solvent or solute.

22. The device according to claim 21, wherein the volume-varying device consists of a pair of cylinder and piston, the cylinder having an inner side surface connected to an opening of the adsorbent;

wherein a predetermined number of openings of the adsorbent are opened or closed according to a position of the piston.

23. The device according to claim 16, further comprising a heating device and/or a carrier-gas introductory port in the vessel for facilitating the vaporizing of at least one of the solvent and the solute.

24. The device according to claim 16, wherein said solvent is a hydrophobic solvent.

25. The device according to claim 16, wherein said solvent is a hydrocarbon solvent.

26. The device according to claim 16, wherein at least one of the solvent and the solute with a lower boiling point or a lower polarity is transferred through the adsorbent.

* * * * *